United States Patent [19]
Zou et al.

[11] Patent Number: 6,051,755
[45] Date of Patent: Apr. 18, 2000

[54] MODIFICATION OF PLANT LIPIDS AND SEED OILS UTILIZING YEAST SLC GENES

[75] Inventors: Jitao Zou; David C. Taylor; Vesna Katavic; Samuel L. MacKenzie; Wilfred A. Keller, all of Saskatoon, Canada

[73] Assignee: National Research Council of Canada, Ottawa, Canada

[21] Appl. No.: 08/973,353

[22] PCT Filed: May 31, 1996

[86] PCT No.: PCT/CA96/00350

§ 371 Date: Nov. 28, 1997

§ 102(e) Date: Nov. 28, 1997

[87] PCT Pub. No.: WO96/38573

PCT Pub. Date: Dec. 5, 1996

[30] Foreign Application Priority Data

May 31, 1996 [GB] United Kingdom .................... 9510927

[51] Int. Cl.[7] ................ A01H 5/00; C12N 15/82

[52] U.S. Cl. ................ 800/281; 800/298; 800/306; 800/312; 800/314; 800/317; 800/320.1; 800/322; 435/252.3; 435/320.1; 435/468

[58] Field of Search ....................... 800/298, 278, 800/281, 306, 314, 320.1, 317, 312, 322; 435/69.1, 419, 430, 252.8, 320.1, 468, 469

*Primary Examiner*—Elizabeth F. McElwain
*Attorney, Agent, or Firm*—J. Wayne Anderson

[57] ABSTRACT

This invention relates to the modification of plant lipids and seed oils by genetic engineering techniques to produce oilseeds of enhanced commercial value. In one form, the invention relates to a transgenic oilseed plant, or a seed of such plant, having a genome incorporating an expressible yeast SLC1-1 or SLC1 gene. The invention also provides a method of producing a transgenic oilseed plant, which comprises introducing into the genome of the plant an expressible yeast SLC1-1 or SLC1 gene. The invention also relates to various plasmids and vectors used in the method of the invention.

24 Claims, 7 Drawing Sheets

SLC1-1 Gene

```
     1                    21                   41
     atgagtgtgataggtaggttcttgtattacttgaggtccgtgttggtcgtactggcgctt
1:   M  S  V  I  G  R  F  L  Y  Y  L  R  S  V  L  V  V  L  A  L
     61                   81                   101
     gcaggctgtggcttttacggtgtaatcgcctctatcctttgcacgttaatcggtaagcaa
21:  A  G  C  G  F  Y  G  V  I  A  S  I  L  C  T  L  I  G  K  Q
     121                  141                  161
     catttggctctgtggattactgcgcgttgttttaccatgtcatgaaattgatgcttggc
41:  H  L  A  L  W  I  T  A  R  C  F  Y  H  V  M  K  L  M  L  G
     181                  201                  221
     cttgacgtcaaggtcgttggcgaggagaatttggccaagaagccatatattatgattgcc
61:  L  D  V  K  V  V  G  E  E  N  L  A  K  K  P  Y  I  M  I  A
     241                  261                  281
     aatcaccaatccaccttggatatcttcatgttaggtaggattttccccccctggttgcaca
81:  N  H  Q  S  T  L  D  I  F  M  L  G  R  I  F  P  P  G  C  T
     301                  321                  341
     gttactgccaagaagtctttgaaatacgtccccttctggggttggttcatggctttgagt
101: V  T  A  K  K  S  L  K  Y  V  P  F  L  G  W  F  M  A  L  S
     361                  381                  401
     ggtacatatttcttagacagatctaaaaggcaagaagccattgacaccttgaataaaggt
121: G  T  Y  F  L  D  R  S  K  R  Q  E  A  I  D  T  L  N  K  G
     421                  441                  461
     ttagaaaatgttaagaaaaacaagcgtgctctatgggttttcctgagggtaccaggtct
141: L  E  N  V  K  K  N  K  R  A  L  W  V  F  P  E  G  T  R  S
     481                  501                  521
     tacacgagtgagctgacaatgttgcctttcaagaagggtgctttccatttggcacaacag
161: Y  T  S  E  L  T  M  L  P  F  K  K  G  A  F  H  L  A  Q  Q
     541                  561                  581
     ggtaagatccccattgttccagtggttgtttccaataccagtactttagtaagtcctaaa
181: G  K  I  P  I  V  P  V  V  V  S  N  T  S  T  L  V  S  P  K
     601                  621                  641
     tatggggtcttcaacagaggctgtatgattgttagaattttaaaacctatttcaaccgag
201: Y  G  V  F  N  R  G  C  M  I  V  R  I  L  K  P  I  S  T  E
     661                  681                  701
     aacttaacaaaggacaaaattggtgaatttgctgaaaaagttagagatcaaatggttgac
221: N  L  T  K  D  K  I  G  E  F  A  E  K  V  R  D  Q  M  V  D
     721                  741                  761
     actttgaaggagattggctactctcccgccatcaacgatacaaccctcccaccacaagct
241: T  L  K  E  I  G  Y  S  P  A  I  N  D  T  T  L  P  P  Q  A
     781                  801                  821
     attgagtatgccgctcttcaacatgacaagaaagtgaacaagaaaatcaagaatgagcct
261: I  E  Y  A  A  L  Q  H  D  K  K  V  N  K  K  I  K  N  E  P
     841                  861                  881
     gtgccttctgtcagcattagcaacgatgtcaatacccataacgaaggttcatctgtaaaa
281: V  P  S  V  S  I  S  N  D  V  N  T  H  N  E  G  S  S  V  K
     901                  921                  941
     aagatgcattaagccaccaccacatttttagagtagtatatagaccc
301: K  M  H  @
```

FIG. 1

SLC1 Gene

```
      1                   21                  41
      atgagtgtgataggtaggttcttgtattacttgaggtccgtgttggtcgtactggcgctt
  1:  M  S  V  I  G  R  F  L  Y  Y  L  R  S  V  L  V  V  L  A  L
      61                  81                  101
      gcaggctgtggcttttacggtgtaatcgcctctatcctttgcacgttaatcggtaagcaa
 21:  A  G  C  G  F  Y  G  V  I  A  S  I  L  C  T  L  I  G  K  Q
      121                 141                 161
      catttggctcagtggattactgcgcgttgttttaccatgtcatgaaattgatgcttggc
 41:  H  L  A  Q  W  I  T  A  R  C  F  Y  H  V  M  K  L  M  L  G
      181                 201                 221
      cttgacgtcaaggtcgttggcgaggagaatttggccaagaagccatatattatgattgcc
 61:  L  D  V  K  V  V  G  E  E  N  L  A  K  K  P  Y  I  M  I  A
      241                 261                 281
      aatcaccaatccaccttggatatcttcatgttaggtaggattttcccccctggttgcaca
 81:  N  H  Q  S  T  L  D  I  F  M  L  G  R  I  F  P  P  G  C  T
      301                 321                 341
      gttactgccaagaagtctttgaaatacgtccccttctgggttggttcatggctttgagt
101:  V  T  A  K  K  S  L  K  Y  V  P  F  L  G  W  F  M  A  L  S
      361                 381                 401
      ggtacatatttcttagacagatctaaaaggcaagaagccattgacaccttgaataaaggt
121:  G  T  Y  F  L  D  R  S  K  R  Q  E  A  I  D  T  L  N  K  G
      421                 441                 461
      ttagaaaatgttaagaaaaacaagcgtgctctatgggttttttcctgagggtaccaggtct
141:  L  E  N  V  K  K  N  K  R  A  L  W  V  F  P  E  G  T  R  S
      481                 501                 521
      tacacgagtgagctgacaatgttgcctttcaagaagggtgctttccatttggcacaacag
161:  Y  T  S  E  L  T  M  L  P  F  K  K  G  A  F  H  L  A  Q  Q
      541                 561                 581
      ggtaagatccccattgttccagtggttgtttccaataccagtactttagtaagtcctaaa
181:  G  K  I  P  I  V  P  V  V  V  S  N  T  S  T  L  V  S  P  K
      601                 621                 641
      tatggggtcttcaacagaggctgtatgattgttagaattttaaaacctatttcaaccgag
201:  Y  G  V  F  N  R  G  C  M  I  V  R  I  L  K  P  I  S  T  E
      661                 681                 701
      aacttaacaaaggacaaaattggtgaatttgctgaaaaagttagagatcaaatggttgac
221:  N  L  T  K  D  K  I  G  E  F  A  E  K  V  R  D  Q  M  V  D
      721                 741                 761
      actttgaaggagattggctactctcccgccatcaacgatacaaccctcccaccacaagct
241:  T  L  K  E  I  G  Y  S  P  A  I  N  D  T  T  L  P  P  Q  A
      781                 801                 821
      attgagtatgccgctcttcaacatgacaagaaagtgaacaagaaaatcaagaatgagcct
261:  I  E  Y  A  A  L  Q  H  D  K  K  V  N  K  K  I  K  N  E  P
      841                 861                 881
      gtgccttctgtcagcattagcaacgatgtcaatacccataacgaaggttcatctgtaaaa
281:  V  P  S  V  S  I  S  N  D  V  N  T  H  N  E  G  S  S  V  K
      901                 921                 941
      aagatgcattaagccaccaccacatttttagagtagtatatagaccc
301:  K  M  H  @
```

FIG. 2

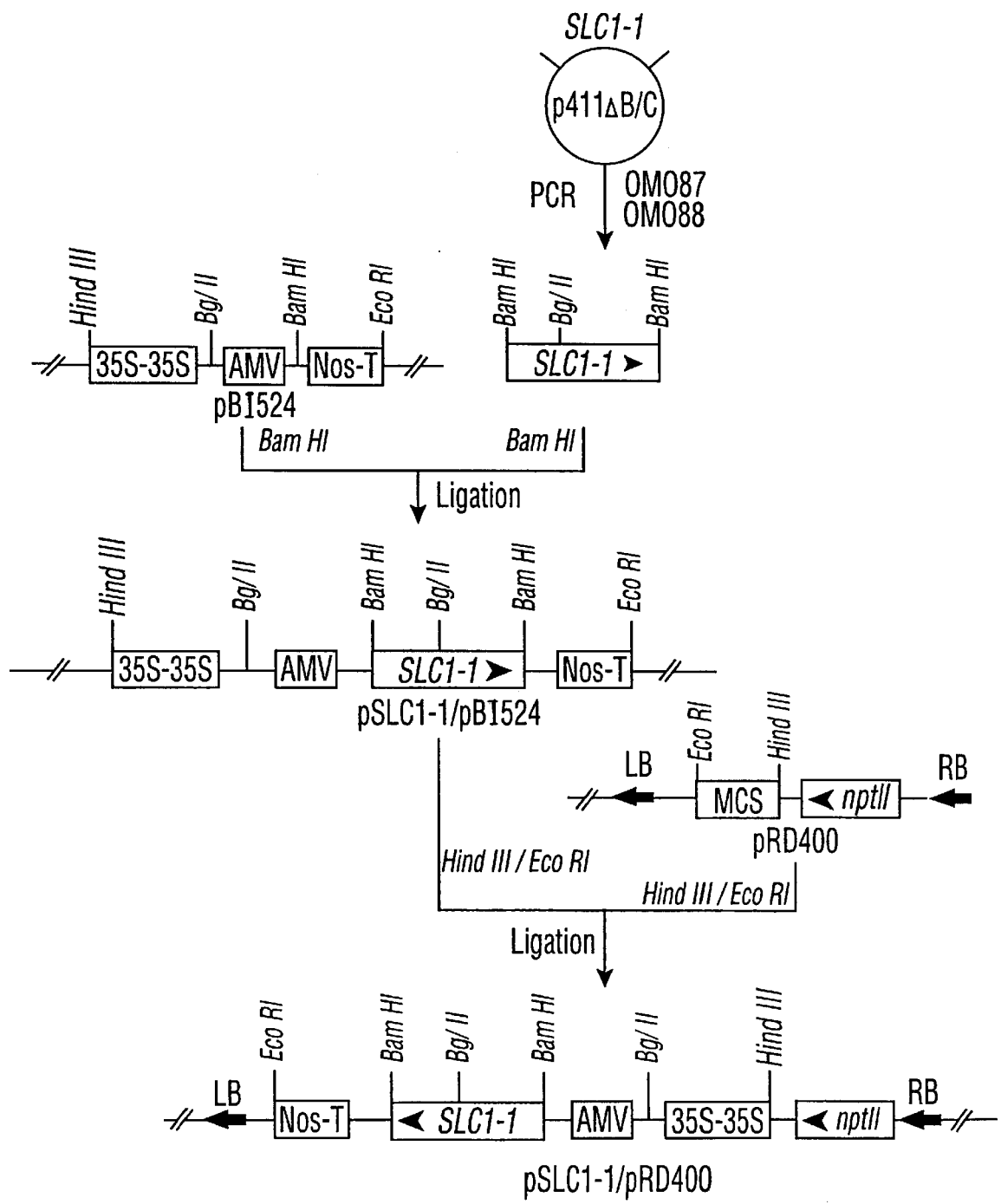
FIG. 3 Cloning strategy for constructing SLC1-1 plant transformation vector (salient features not drawn to scale)

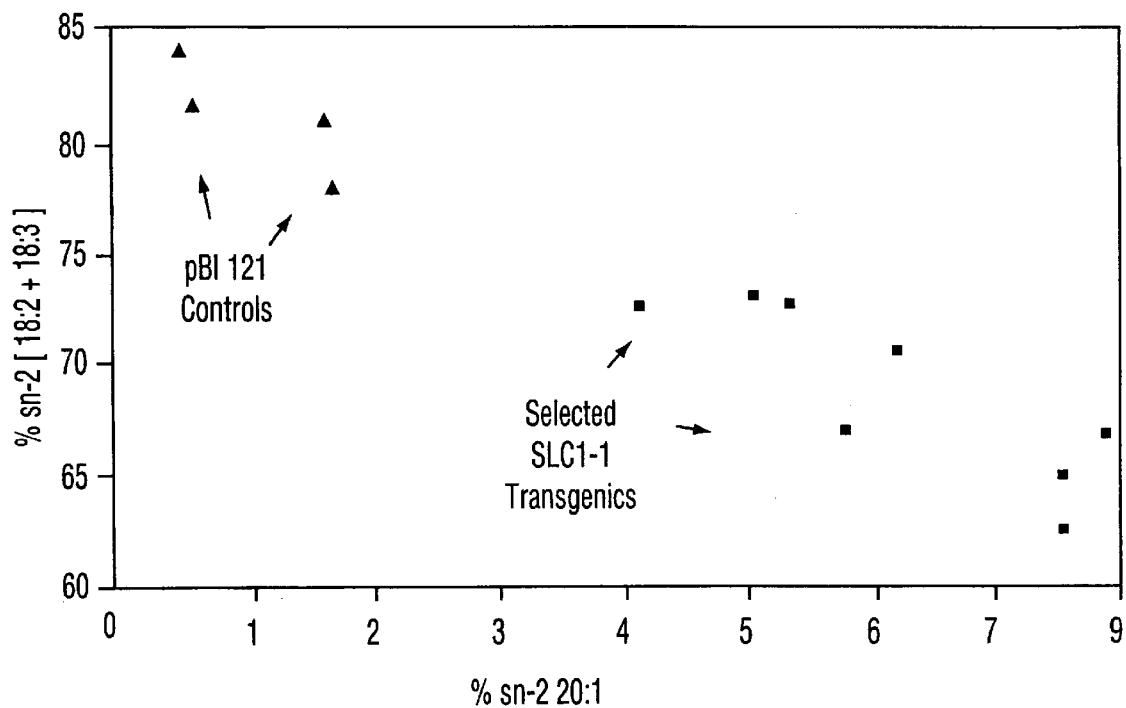
FIG. 4 Correlation between decrease in *sn-2* polyunsaturated fatty acids and increase in *sn-2* eicosenoic acid in A. *thaliana* Control and *SLC1-1* Transgenic $T_3$ Seeds.

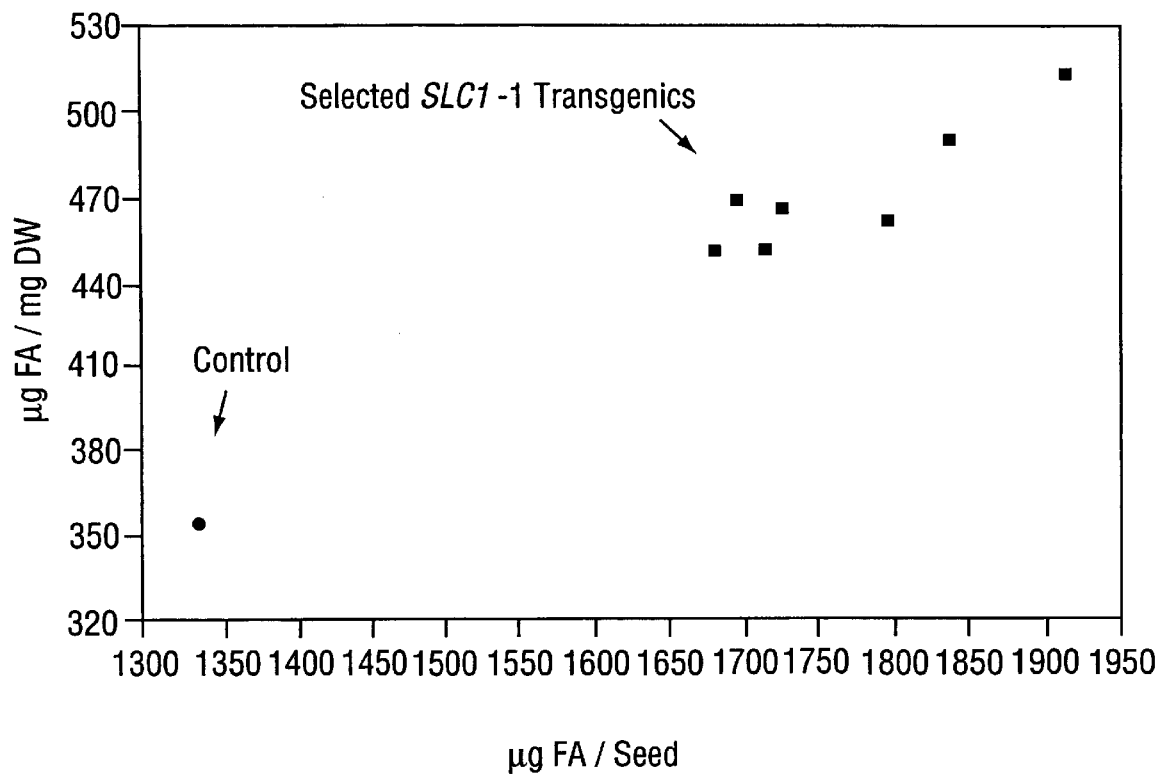
FIG. 5 Correlation of "Fatty Acid Content / Seed" and "Fatty Acid Content / mg Dry Weight" in Untransformed Control and Selected *SLC1-1* Transgenics of *B. napus* cv HERO (12 - Seed Samples)

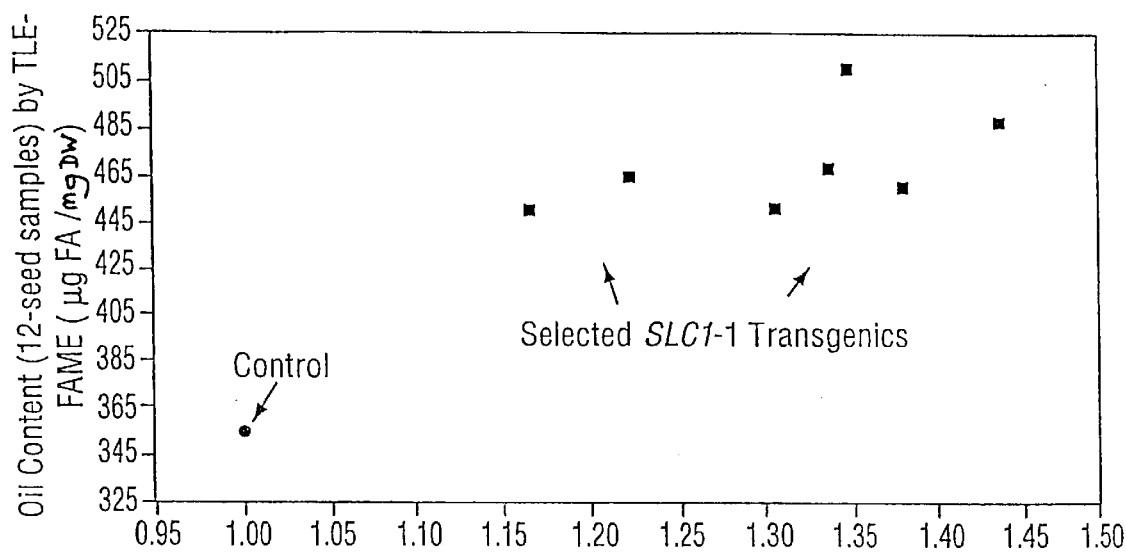
FIG. 6 Correlation Between Relative Oil Content Estimated by $^1$H-NMR (non-destructive) Method vs. TLE-FAME (destructive) Method in Untransformed Control and Selected *SLC1-1* Transgenics of *B. napus* cv HERO

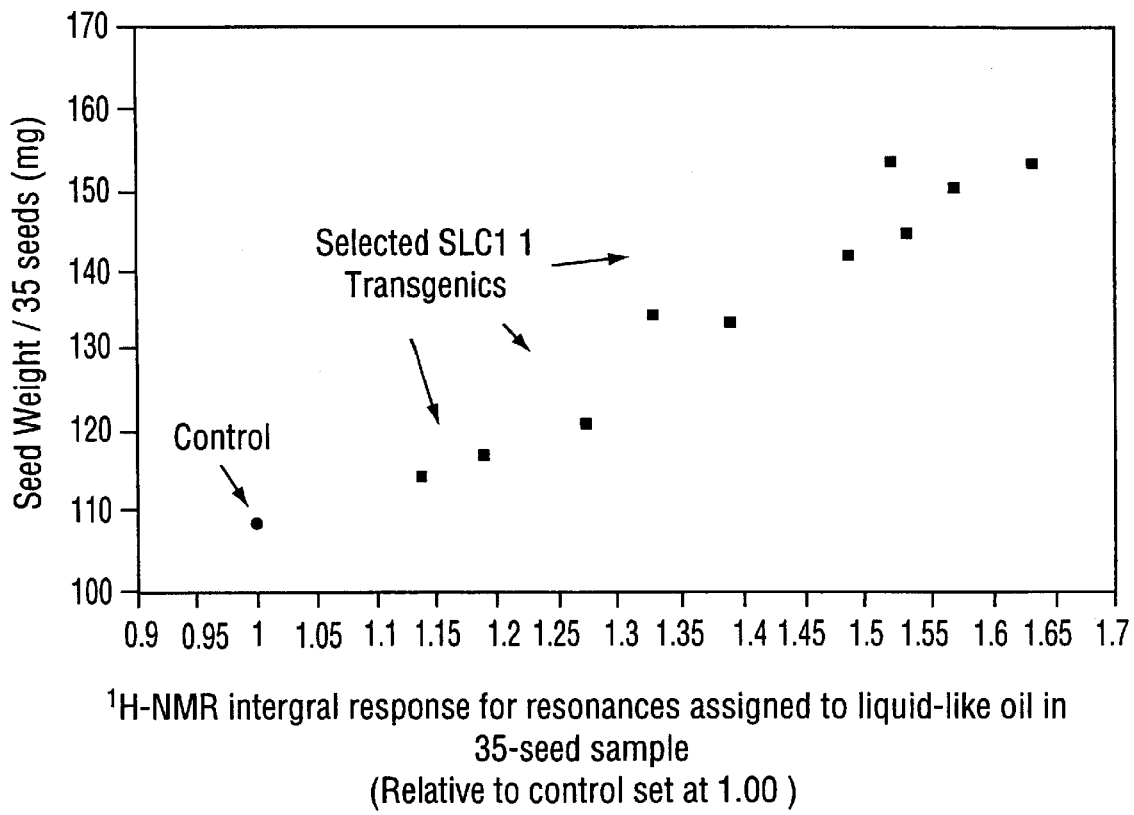
FIG. 7 Correlation Between Seed Dry Weight and Oil Content (estimated by the non-destructive $^1$H-NMR method) in Untransformed Control and Selected *SLC1-1* Transgenics of *B. napus* cv HERO

MODIFICATION OF PLANT LIPIDS AND SEED OILS UTILIZING YEAST SLC GENES

TECHNICAL FIELD

This invention relates to the modification of plant lipids and seed oils by genetic engineering techniques. More particularly, the invention relates to a method of genetically modifying oilseed plants to produce oilseeds or whole plants of enhanced commercial value. The invention also relates to the modified plants and seeds, and to genetic materials and vectors used for the production of such plants, and for further modifications of plants.

BACKGROUND ART

There is considerable interest nowadays in modifying the seed oil fatty acid composition and content of oilseeds by molecular genetic means to provide a dependable source of Super High Erucic Acid Rapeseed (SHEAR) oil for use as an industrial feedstock. A similar interest exists for producing other strategic non-edible oils (e.g. seed oils high in hydroxy-, epoxy-, short and medium chain fatty acids, etc.) in traditional oilseed crops (e.g. rapeseed, flax, sunflower, soybean).

For edible oils, there is considerable interest in changing the fatty acid composition (e.g. higher oleic/lower polyunsaturates, lower saturates, higher saturates) as well as increasing the oil content in oilseed crops such as Canola and edible oil flax (Linola), soybean and sunflower.

Currently, there are no documented demonstrations of increases in oil content (yield) by transgenic means, although yield increases by traditional breeding and selection continue to bring about incremental improvements.

In contrast, increases in the proportions of some strategic fatty acids have been achieved by the introduction of various plant fatty acid biosynthesis and acyltransferase genes in oilseeds. Some examples of such processes are the following:

1. Expression of a medium chain fatty acyl-ACP thioesterase from California Bay, in Brassicaceae to increase the lauric acid (12:0) content (Calgene; Voelker et al., 1992; 1996—see References 35 and 36 in the accompanying "References Pertinent to the Present Invention").
2. Expression of a Jojoba β-ketoacyl-CoA synthase in low erucic acid *Brassica napus* (Canola) cultivars to increase the level of erucic acid; the effect following expression in high erucic acid cultivars was negligible (Calgene; Lassner et al., 1996—see Reference 20).
3. Expression of an anti-sense construct to the stearoyl-ACP Δ9 desaturase in Brassicaceae to increase the stearic acid content (Calgene; Knutzon et al., 1992—see Reference 16).
4. Increased proportions of oleic acid in *B. napus* by co-suppression using a sense construct encoding plant microsomal FAD2 (Δ12) desaturase (duPont/InterMountain Canola; Hitz et al., 1995—see Reference 12).
5. Increased proportions of 12:0 or 22:1 in the sn-2 position of triacylglycerols (TAGs) in rapeseed by expression of coconut or meadowfoam lysophosphatidic acid acyltransferases (LPATs; E.C. 2.3.1.51), respectively (Calgene; Knutzon et al., 1995 a & b;—see References 17 and 18; Lassner et al., 1995—see Reference 21).

Although the use of plant transgenes resulted in altered proportions of sn-2 lauric and erucic acids, in laurate canola and high erucic acid rapeseed, respectively, the overall proportions of lauric and erucic acids in the seed oil were not increased, and there was no evidence of increased total fatty acid content, or increased oil yield in these transgenics.

There is accordingly a need for new ways of increasing oil yield and improving oil composition in oilseed plants by employing genetic engineering techniques.

DISCLOSURE OF INVENTION

An object of the present invention is to genetically modify oilseed plants to improve the commercial value of such plants, the seeds of such plants, and the oils produced from such plants.

Another object of the invention is to provide a method of modifying the yield and composition of oils derived from oilseed plants.

The present invention is based on the discovery that sn-2 acylglyceride fatty acyltransferase genes (SLC1-1 and its allele, SLC1) from yeast (*Saccharomyces cereviseae*), can be used to change the oil content and oil composition of plant seed and leaf lipids.

Thus, according to one aspect of the present invention, there is provided a transgenic oilseed plant having a genome incorporating an expressible yeast SLC1-1 or SLC1 gene.

According to another aspect of the invention, there is provided a seed of a transgenic oilseed plant having a genome incorporating an expressible yeast SLC1-1 or SLC1 gene.

According to yet another aspect of the invention, there is provided a method of producing a transgenic oilseed plant, which comprises introducing into the genome of said plant an expressible yeast SLC1-1 or SLC1 gene.

The invention also relates to various plasmids and vectors used in the method of the invention, and to the co-introduction of other genes into plants modified to include the SLC1-1 and SLC1 genes.

The advantages of the present invention include the fact that the yeast SLC1-1 and SLC1 genes can be used to increase the oil content and to change total fatty acid composition, as well as to alter the acyl composition of TAGs, including the sn-2 position, and to change the relative proportions of TAG species, in various oilseed plants, e.g. *Arabidopsis thaliana,* in high erucic acid and canola cultivates of *Brassica napus,* and in *Brassica carinata.*

Moreover, the yeast sn-2 acyltransferase (SLC1-1 and SLC1 genes) can be utilized in high erucic acid Brassicaceae to increase the oil content and to produce seed oils with increased content of very long-chain fatty acids (VLCFAs) and TAGs with an altered stereospecific composition with respect to very long chain fatty acids. Thus, in contrast to previous results utilizing plant transgenes (as mentioned above), the current invention utilizing a yeast transgene is capable of achieving combined increases in seed oil content, seed erucic acid content and overall proportions of erucic acid in the seed oil.

The yeast sn-2 acyltransferase (SLC1-1 and SLC1 genes) can also be utilized in edible oil cultivars (Canola-quality cultivars) of the Brassicaceae, to increase the oil content and to produce seed oils with altered proportions of oleic acid, polyunsaturated fatty acids and very long chain saturated fatty acids.

The related yeast SLC1-1 and SLC1 alleles can be utilized in the same ways. Both alleles encode an sn-2 acyltransferase; SLC1 differs from SLC1-1 only in the amino acid at position 44 (Glutamine, Q) compared to SLC1-1, where the amino acid at position 44 is Leucine (L).

The SLC1-1 and SLC1 transgenic plants can be used as host germplasm for further down-regulation of endogenous plant acyltransferases.

To achieve directed assembly of TAG biosynthesis to produce stereospecifically-designed TAGs, the co-ordinated expression of a number of biochemical reactions, including that mediated by LPAT, is required. One of the distinct possibilities with respect to optimizing transgenic expression of foreign LPATs to synthesize TAGs with new acyl composition (e.g. increased very long chain fatty acids at the sn-2 position), is the possible need to simultaneously down-regulate the endogenous LPAT already present in the transgenic host (e.g. an LPAT which normally prefers to insert polyunsaturated $C_{18}$ fatty acyl groups into the sn-2 position). The overall homologies between the yeast sn-2 acyltransferases and published plant sn-2 acyltransferases (LPATs) are low, and are restricted mostly to the C-termini of the proteins. In contrast, the plant acyltransferases have much greater overall homology to each other, and regions of homology extend throughout the sequence. Therefore, the use of the yeast SLC genes to achieve the effects described herein, allow a unique opportunity to further improve these traits in a way not possible when the initial transformation was performed with a plant acyltransferase. In effect, the limited homology between plant and the yeast sn-2 acyltransferases are low enough to allow strategies to down-regulate the host plant LPAT by conventional means (e.g. anti-sense RNA technology or a co-suppression phenomenon; Mol et al., 1990; Van Blokland et al., 1993; De Lange et al., 1995) without a concomitant negative impact on the expression of the yeast transgene or on plant seed development. Thus, the yeast transgene strategy has a distinct advantage over that in which another plant transgene is introduced into a host plant where there is a highly homologous, endogenous LPAT.

The yeast sn-2 acyltransferase (SLC1-1 and SLC1 genes) can be used to increase the oil content and alter the acyl composition of TAGs in all other oilseeds including borage (Borago spp.), castor (*Ricinus communis*), cocoa bean (*Theobroma cacao*), corn (*Zea mays*), cotton (Gossypium spp), Crambe spp., Cuphea spp., flax (Linum spp.), Lesquerella and Limnanthes spp., nasturtium (Tropaeolum spp.), Oenothera spp., olive (Olea spp.), palm (Elaeis spp.), peanut (Arachis spp.), safflower (Carthamus spp.), soybean (Glycine and Soja spp.), sunflower (Helianthus spp.), tobacco (Nicotiana spp.) and Vernonia spp.

The yeast sn-2 acyltransferase (SLC1-1 and SLC1 genes) oilseed transformants can be utilized, by a second transformation, with all other value-added fatty acid biosynthesis genes (e.g. the hydroxylase gene from castor or Lesquerella spp.), or by crossing with related oilseed transformants already containing such value-added genes, to produce seed oils with increased amounts of value-added fatty acids (e.g. increased hydroxy fatty acid content and altered TAG composition with respect to those containing hydroxy fatty acids).

The SLC1-1 gene and related SLC1 allele, can be utilized to modify fatty acid and lipid profiles in vegetative tissues to improve tolerance to biotic and abiotic plant stresses (e.g. increased membrane fluidity in root and leaf tissues to improve frost tolerance).

The use of the yeast SLC1-1 gene and the SLC1 allele in plants, to bring about changes in overall lipid content and composition, has not been previously disclosed or demonstrated (reduced to practice) as a means for manipulating the relative proportions or amounts of fatty acids (e.g. very long chain fatty acids), and also for increasing the oil content of crops producing edible or industrial oils.

Previously, there have been no demonstrations of increases in oil yields brought about by transgenic means. More specifically, there was no previous evidence that yeast acyltransferases, the enzymes responsible for synthesizing triacylglycerols, have been expressed in plants to alter oil composition or content.

In contrast, however, a decrease in diacylglycerol acyltransferase activity in a mutant of *Arabidopsis thaliana* resulted in a decrease in oil yield and a change in acyl composition (Katavic et al., (1995) *Plant Physiology*, 108:399–409—see Reference 15).

BRIEF DESCRIPTION OF THE DRAWINGS

FIG. 1 shows the nucleotide [SEQ ID NO:1] and deduced amino acid sequence [SEQ ID NO:2] of the coding region of the yeast SLC1-1 gene used in the present invention, the stop codon being identified by "@", and a highly conserved consensus sequence among bacterial and yeast sn-2 acyltransferases being underlined;

FIG. 2 shows the nucleotide [SEQ ID NO:3] and deduced amino acid sequence [SEQ ID NO:4] of the coding region of the yeast SLC1 gene used in the present invention, the stop codon being identified by "@", and a highly conserved consensus sequence among bacterial and yeast sn-2 acyltransferases being underlined;

FIG. 3 shows a strategy for constructing an SLC1-1 plant transformation vector explained in the Experimental Details provided later, the salient features not being drawn to scale; and FIGS. 4 to 7, as well as Tables 1–20 below, show the results of tests explained in the Experimental Details provided later.

BEST MODES FOR CARRYING OUT THE INVENTION

The sequences of the SLC1-1 gene [SEQ ID NO:1] and the SLC1 allele [SEQ ID NO:3], and their derived peptide structures [SEQ ID NOS: 2 and 4], are as shown in FIGS. 1 and 2, respectively.

The yeast SLC1 gene (and related SLC1-1 suppressor allele gene) have been characterized in two publications, as follows (the disclosures of which are incorporated herein by reference);

1. Lester, R. L., Wells, G. B., Oxford, G. and Dickson, R. C. (1993) Mutant strains of *Saccharomyces cerevisiae* lacking sphingolipids synthesize novel inositol glycerolipids that mimic sphingolipid structures. *J. Biol. Chem.* 268: 845–856—Reference 22; and 2. Nagiec, M. M., Wells, G. B., Lester, R. L., and Dickson, R. C. (1993) A suppressor gene that enables *Saccharomyces cerevisiae* to grow without making sphingolipids encodes a protein that resembles an *Escherichia coli* fatty acyltransferase. *J. Biol. Chem.* 268: 22156–22163—Reference 25.

The DNA and amino acid sequences for the coding region of the SLC1-1 gene are stored in GenBank/EMBL under accession No. L13282 (the stored sequence including a 5' untranslated region not disclosed in the present application).

The SLC1 gene was originally cloned from a yeast mutant lacking the ability to make sphingolipids. The mutant allele of SLC1 was shown to encode a protein which suppresses the genetic defect in sphingolipid long chain base biosynthesis. The gene sequence of SLC1 is homologous to the *E.* coli PLSC gene, which has been claimed to encode lysophosphatidic acid acyltransferase (LPAT; and acyltransferase acylating the sn-2 position of lyso-phosphatidic acid (LPA) to give phosphatidic acid (PA)). The SLC1 gene was able to complement the growth defect in JC201 (an *E. coli* strain mutated in PLSC). Based on the observation that SLC strains grown in the absence of long chain base make novel phosphatidylinositol derivatives (Lester et al., (1993) J. Biol. Chem. 268: 845–856.), one possible conclusion by the authors was that the SLC1 encodes a protein capable of acylating the sn-2 position of inositol-containing glycerolipids (i.e. perhaps an lyso-phosphatidyl-inositol acyltransferase, LPIT). Based on these findings, it was reported that SLC1 encodes a yeast sn-2 acyltransferase. However, the authors of the paper (Dickson, Lester et al.), were unable to detect LPAT activity in the complemented *E. coli* JC201 mutant.

In the Nagiec et al. paper, the authors also reported the sequence of the gene for a suppressor allele designated SLC1-1 in which nucleotide 131 has a T instead of an A, resulting in an amino acid change at position 44, from a glutamine to a leucine. The working hypothesis is that the SLC1-1 suppressor allele encodes a variant acyltransferase with an altered substrate specificity, which enables it to use a very long-chain fatty acid (26:0) to acylate the sn-2 position of inositol-containing glycerolipids. The authors have not, to date, provided conclusive evidence of activity encoded by SLC1-1 or SLC1.

Based on the interest of the inventors of the present invention in modifying the very long-chain fatty acid (VLCFA) content of Brassicaceae, the inventors obtained plasmid p411 ΔB/C containing the SLC1-1 suppressor allele gene from Dr. Dickson at the University of Kentucky, Lexington, Ky., USA. The inventors also believed that expressing the foreign gene in a plant might lead to more information in the nature of what SLC1-1 and SLC1 encode. Work carried out by the inventors identified, for the first time, using the model oilseed *Arabidopsis thaliana*, transformants with increased seed oil content, and increased proportions of TAGs containing very long-chain fatty acids (VLCFAs=>$C_{18}$). In addition, there are increased proportions of VLCFAs at the sn-2 position of TAGs, and a concomitant decrease in the proportion of polyunsaturated fatty acids esterified at this position. SLC1-1 transformants of *B. napus* cv. Hero and *B. carinata* (both high erucic acid cultivars) show increased oil content and increased erucic acid content/mg dry weight (DW) of seed. SLC1-1 transformants of *B. napus* cv. Westar (Canola-quality cultivar) show increased proportions of oleic acid (18:1) and decreased proportions of polyunsaturated fatty acids (18:2 and 18:3).

The SLC1-1 and SLC1 genes can be introduced into the genomes of oilseed plants and expressed using conventional genetic engineering techniques. For example, transformation could involve the use of Agrobacterium Ti plasmid-mediated transformation (e.g. in planta, vacuum infiltration, cotyledonary or hypocotyl petiole wound infection, or particle bombardment, etc). Constructs may be driven by constitutive or tissue-specific promoters, as will be apparent to persons skilled in the art.

Broad applicability of the invention to oilseed plants of various kinds is to be expected because oil synthesis follows the same or closely related biochemical pathways in all such plants (see References 29, 30, 37, 38, 39 and 40).

The present invention will be described in more detail with reference to the following experimental details, which provide specific illustration. It should be kept in mind, however, that the present invention is not limited to the details presented below.

EXPERIMENTAL DETAILS

CONSTRUCTION OF VECTORS FOR SLC1-1 TRANSFORMATION

Following the cloning strategy illustrated in FIG. 3 of the accompanying drawings, two primers with 5' BamHI restriction site extensions, OM087 (AGAGAGAGGGATCCATGAGTGTGATAGGTAGG) [SEQ ID NO: 5] and OM088 (GAGGAAGAAGGATCCGGGTCTATATACTACTCT) [SEQ ID NO:6], designed according to the 5' and 3' end sequences of the SLC1 gene [SEQ ID NO:3], respectively, were used in a Polymerase Chain Reaction (PCR) with plasmid p411ΔB/C (obtained from Dr. Dickson at the University of Kentucky, Lexington, Ky., USA), harboring the suppressor allele of the SLC gene (SLC1-1) as template, to generate the SLC1-1 PCR fragment with a BamHI site at both ends. The (SLC1-1) PCR fragment, therefore, represents the suppressor allele of the SLC1 gene with nucleotide T substituting for nucleotide A at position 131, resulting in an amino acid residue change from glutamine to leucine at residue 44. The fragment was digested with BamHI and ligated into the BamHI cloning site located between the tandem 35S promoter and NOS terminator in vector PBI524 (obtained from Dr. Raju S. S. Datla, NRC Plant Biotechnology Institute, 110 Gymnasium Place, Saskatoon, Saskatchewan, Canada, S7N OW9; published by Datla et al., 1993—see Reference 9) to give vector SLC1-1-pBI-524. The orientation of SLC1-1 in the vector SLC1-1-pBI-524 was verified by restriction digestion with BglII which cuts SLC1-1 at nt 377 from the 5' end and immediately downstream of the 35S promoter in vector pBI524. The translation initiation codon of SLC1-1 is maintained, and hence the construct is a transcriptional fusion. The HindIII and EcoRI fragment containing a tandem 35S promoter, AMV enhancer, SLC1-1 encoding sequence and NOS terminator was freed from SLC1-1-pBI-524, and cloned into the EcoRI-HindIII site of vector RD400 (also obtained from Dr. R. Datla; published by Datla et al., 1992—see Reference 8). The final vector pSLC1-1/pRD400 (deposited on May 9, 1996 under the terms of the Budpest Treaty at the American Type Culture Collection, 10801 University Blvd., Manassas, Va. 20110-2209, USA; under deposit no ATCC 97545) was introduced into *Agrobacterium tumefaciens* strain GV3101 (bearing helper plasmid pMP90; Koncz and Schell, 1986) by electroporation.

MOLECULAR BIOLOGICAL TECHNIQUES

Unless otherwise stated, all molecular biological techniques were carried out by methods generally prescribed by Ausubel et al., (1995).

PLANT GROWTH CONDITIONS

All *A. thaliana* control and transgenic plants were grown at the same time, in controlled growth chambers, under continuous fluorescent illumination (150–200 $\mu$E·m$^{-2}$·sec$^{-1}$) at 22° C., as described by Katavic et al., (1995). All other control and transgenic plants of the Brassicaceae (*B. napus, B. carinata*) were grown at the same time, in the P.B.I. Transgenic Plant Center greenhouse under natural light supplemented with high pressure sodium lamps (HPS lamps) with a 16 hour photoperiod (16 h light/8 h dark), at 22° C., and a relative humidity of 25–30%.

PLANT TRANSFORMATION

The SLC1-1/RD400 construct was tested in *A. thaliana* by in planta transformation techniques, and in both high and low erucic acid *B. napus* cultivars, and *B. carinata* (by co-cultivation transformation of cotyledonary petioles and hypocotyl explants with *A. tumefaciens* bearing the SLC1-1 construct).

Testing the SLC1-1 construct in *A. thaliana*

Wild type (WT) *A. thaliana* plants of ecotype Columbia were grown in soil. In planta transformation was performed by wound inoculation (Katavic et al. 1994) or vacuum infiltration (Bechtold et al. 1993) with overnight bacterial suspension of *A. tumefaciens* strain GV3101 bearing helper nopaline plasmid pMP90 (disarmed Ti plasmid with intact vir region acting in trans, gentamycin and kanamycin selection markers; Koncz and Schell (1986)) and binary vector pSLC1-1/pRD400.

After inoculation or infiltration, plants were grown to set seeds ($T_1$). Dry seeds ($T_1$) were harvested in bulk and screened on selective medium with 50 mg/L kanamycin. After two to three weeks on selective medium, seedlings were transferred to soil. Lead DNA was isolated from kanamycin-resistant $T_1$ plants and analysed by PCR amplification of the SLC1-1 fragment. Developing leaves from $T_1$ plants as well as $T_2$ mature seeds from SLC1-1 transgenic lines were used for lipid and biochemical analyses. Developing leaves and mature seeds from untransformed wild type (WT) Columbia plants and pBI121 transgenic plants (binary vector pBI121, containing only kanamycin selection marker and GUS reporter gene; Jefferson et al., 1987) were used as controls in analyses of seed lipids. Based on these analyses, $T_2$ seeds of lines exhibiting changed acyl composition and/or lipid content were grown on selective medium (to eliminate homozygous WT segregants) and then transferred to soil to yield $T_3$ seed populations.

Testing the SLC1-1 construct in *Brassica napus* and *Brassica carinate*:

Transformation experiments were also performed on *B. napus* cv. Westar (canola variety, low erucic acid), *B. napus* cvs. Hero, Reston and Argentine (all high erucic acid varieties) and *B. carinata* (breeding line C90-1163, a high erucic acid line) by co-cultivation of cotyledonary petioles and hypocotyl explants with *A. tumefaciens* bearing the SLC1-1/RD400 construct. Transformation methods according to Moloney et al.(1989) and DeBlock et al.(1989) were modified to optimize transformation conditions.

Modifications of the cotyledonary-petiole transformation method (Moloney et al., 1989) included the introduction of a 7-day explant-recovery period following co-cultivation, on MS medium with the hormone benzyladenine (BA) and the antibiotic timentin, for elimination of Agrobacterium.

Modifications of the hypocotyl-explant transformation method (DeBlock et al.; 1989) included: (1) preculture of explants on agar-solidified MS medium with the hormones 2,4-dichlorophenoxyacetic acid (2,4-D) and kinetin (K); (2) co-cultivation of hypocotyl explants with Agrobacterium in petri dishes with the same medium as for preculture, on sterile filter paper; (3) following co-cultivation, a 7-day explant-recovery period on medium with hormones (2,4-D and K), and with timentin for Agrobacterium elimination, (4) regeneration of transgenic shoots on MS medium with the hormones benzyladenine (BA) and zeatin (Z), the ethylene inhibitor silver nitrate ($AgNO_3$), and antibiotics timentin (for Agrobacterium elimination) and kanamycin (for transformed-cell/shoot selection).

Green shoots were rooted and transferred to soil. Genomic DNA was isolated from developing leaves and PCR analyses and Southern analyses (Southern, 1975) were performed. Seeds ($T_1$) from transgenic plants were har vested and from each transgenic line, ten $T_1$ plants were grown in soil. Mature seeds ($T_2$) from these plants were harvested and subjected to lipid and biochemical analyses.

LIPID ANALYSES AND ACYLTRANSFERASE (LPAT) ASSAYS

Analyses of Leaf and Seed Lipids from SLC1-1 and WT/pBI121 Transgenics and Untransformed WT plants Lipids were isolated from mature seed and developing leaves as described previously (Taylor et al., 1992; Katavic et al, 1995) and analyzed by GC for total fatty acid content and fatty acid composition. Triacylglycerol species were analyzed by high-temperature GC as described by Katavic et al., 1995. Stereospecific analyses of TAGs were performed on intact seed lipids (chiefly TAGs) as described by Taylor et al., 1994, 1995 a & b).

LPAT assays

For leaf assays, leaves at mid-expansion were chosen from control and SLC1-1 transgenic plants, and leaf tissue sampled from several leaves with a cork-borer. For developing seed assays, in *A. thaliana* 25–30 silques were harvested at mid-seed development (15–18 d.p.a.) to give developing $T_3$ seed samples from both controls (untransformed WT and pBI121-transformed) and selected SLC1-1 transgenics. *B. napus* and *B. carinata* $T_2$ embryos at the mid cotyledonary stage of development were harvested from 3 siliques of control and selected SLC1-1 transgenic plants. All plant material was frozen immediately in liquid nitrogen and stored at $-70°$ C. until homogenized. Homogenates of both plant leaf and developing seed tissues were prepared and LPAT assays conducted as described by Taylor et al., (1995b).

All protocols with respect to yeast strains were carried out as described by Ausubel et al., (1995, Unit 13.1 *Basic Techniques of Yeast Genetics*). Wild-type *S. cerevisiae* and *S. pombe* strains were cultured in YPD medium at 28° C. at 270 r.p.m. overnight. At mid-log phase, cells were sampled, pelleted by centrifugation at 5,000 r.p.m. for 5 min, and resuspended in 100 mM Hepes-NaOH, pH 7.4. Cell lysates were prepared using acid-washed glass beads as described by Ausubel et al., 1995 (Unit 13.1, Section 13.13.4).

LPAT assays were conducted at pH 7.4, with shaking at 100 r.p.m., in a water bath at 30° C. for 10–30 min. Assay mixtures (0.5 mL final volume) contained protein (10–200 $\mu$g, depending on the tissue/extract), 90 mM Hepes-NaOH, 0.5 mM ATP, 0.5 mM CoASH, 2 mM spermidine, 45 $\mu$M 18:1-LPA, and either 18 $\mu$M [1-$^{14}$C]-18:1-CoA, [1-$^{14}$C]-20:1-CoA, or [1-$^{14}$C]-22:1-CoA (each at a specific activity of 10 nCi/nmol) as the acyl donor. All other conditions for the measurement of LPAT activity are as detailed in Taylor et al (1995b).

$^1$H-NMR of Mature Seeds $^1$H-NMR analyses for relative oil yield (Alexander et al., 1967; Rutar, 1989) were carried out on intact seeds of control and SLC1-1-transformed *B. napus* cv. Hero, and *B. carinata*, using a Bruker AM wide-bore spectrometer operating at 360 MHz. To reduce anisotropic line broadening, the seeds (35/sample) were rotated at 1 kHz in a zirconium rotor oriented 54.7° to the magnetic field (magic angle sample spinning, MASS).

RESULTS

Acyl-CoA Specificity of Yeast (*S. ceriviseae; S. pombe*) sn-2 Acyltransferase (LPAT)

Yeast cell lysates from both *S. cerevisae* and *S. pombe* were assayed for relative sn-2 acyltransferase activity utilizing 18:1 LPA as an acyl acceptor and different radiolabeled acyl-CoAs. The acyl-CoA specificity of the yeast LPATs in vitro was quite broad, and the LPAT was capable of inserting both endogenous (16:0, 18:1) and non-endogenous (18:2, 18:3, 20:1, 22:1 and ricinoleoyl) acyl groups into the sn-2 position of 18:1 LPA, as shown in Table 1 below:

TABLE 1

Relative *S. cerevisiae* and *S. pombe* acyl-CoA:
LPAT activities using 45 μM 18:1-LPA
as acyl acceptor

| $^{14}$C-Acyl-CoA supplied (18 μM) | LPAT Activity nmol/min/mg protein | LPAT Activity relative to 18:1-CoA (%) |
|---|---|---|
| *S. cerevisiae* | | |
| 18:1-CoA | 3.75 | 100 |
| 18:2-CoA | 3.54 | 94.5 |

TABLE 1-continued

Relative *S. cerevisiae* and *S. pombe* acyl-CoA:
LPAT activities using 45 μM 18:1-LPA
as acyl acceptor

| $^{14}$C-Acyl-CoA supplied (18 μM) | LPAT Activity nmol/min/mg protein | LPAT Activity relative to 18:1-CoA (%) |
|---|---|---|
| 18:1 Δ12-OH—CoA | 1.90 | 50.7 |
| 20:1-CoA | 1.92 | 51.3 |
| 22:1-CoA | 0.33 | 8.9 |
| *S. pombe* | | |
| 18:1-CoA | 1.50 | 100 |
| 18:2-CoA | 1.27 | 84.7 |
| 18:1 Δ12-OH—CoA | 0.85 | 56.7 |
| 20:1-CoA | 0.38 | 25.3 |
| 22:1-CoA | 0.60 | 40.0 |

Because the yeast LPAT (sn-2 acyltransferase) has a relatively broad specificity, transformation of oilseeds rich in very long-chain fatty acids (*A. thaliana, B. napus*) with the yeast SLC1-1 gene can be predicted to result in enriched VLCFA content, including the sn-2 position. In addition, yeast SLC1 and SLC1-1 transformants can be predicted to be excellent hosts for transformation with hydroxylase genes from castor (*R. communis*) and Lesquerella spp. to produce seed oils enriched in hydroxy fatty acids. Alternatively, hydroxylase transformants may be sexually crossed with SLC1-1 or SLC1 transformants.

*A. thaliana* SLC1-1 Transformant Seed Lipid Analyses:

Data from *Arabidopsis thaliana* transformation indicates that the gene has a dramatic effect on the total seed lipid content and sn-2 composition of TAGs. A large number of SLC1-1 $T_2$ transgenic lines (21 of 48) showed significantly increased oil yields over untransformed controls, and pBI121 (without SLC1-1 insert) controls, as shown in Table 2 below:

TABLE 2

Seed fatty acid contents of untransformed wild-type (u-WT) *A. thaliana*, pB1121(-SLC1-1)
*A. thaliana* transformants (Controls) and selected $T_2$ transgenic lines of
*A. thaliana* transformed with the yeast SLC1-1 gene.
(Values are fatty acid content (μg)/50 seeds).

| Line | 16:0 | 18:0 | 10:1 c9 | 18:1 c11 | 18:2 | 18:3 | 20:0 | 20:1 | 20:2 | 22:0 | 22:1 | 24:0 + 24:1 | Total |
|---|---|---|---|---|---|---|---|---|---|---|---|---|---|
| u-WT Control | 28.2 | 12.2 | 50.5 | 5.7 | 101.1 | 71.9 | 7.7 | 74.8 | 8.7 | 1.9 | 8.3 | 1.3 | 372.5 |
| pBI121 Control | 28.4 | 12.4 | 50.2 | 4.1 | 99.9 | 66.2 | 6.7 | 74.0 | 7.1 | tr* | 7.2 | tr* | 360.2 |
| 3 | 28.8 | 12.3 | 57.4 | 5.7 | 114.1 | 78.8 | 7.7 | 82.5 | 9.6 | 5.7 | 8.6 | 1.7 | 412.3 |
| 7 | 37.1 | 18.4 | 102.9 | 5.9 | 111.6 | 84.4 | 7.6 | 71.8 | 8.0 | 2.9 | 7.7 | 2.7 | 461.0 |
| 16 | 33.0 | 12.5 | 62.0 | 6.2 | 131.7 | 95.0 | 9.0 | 96.4 | 12.6 | 1.7 | 11.0 | 2.0 | 473.0 |
| 20 | 36.3 | 16.1 | 87.7 | 7.6 | 153.3 | 95.9 | 10.7 | 118.8 | 11.6 | 2.5 | 12.4 | 3.3 | 556.4 |
| 21 | 32.1 | 14.6 | 62.5 | 6.2 | 121.3 | 89.1 | 9.4 | 89.3 | 9.9 | 2.2 | 9.7 | 2.4 | 448.5 |
| 22 | 31.9 | 13.0 | 57.3 | 5.9 | 113.9 | 86.7 | 8.6 | 85.8 | 10.2 | 1.7 | 9.6 | 2.0 | 426.5 |
| 23 | 35.4 | 15.7 | 72.5 | 7.5 | 139.7 | 95.6 | 10.5 | 106.9 | 12.5 | 2.3 | 11.7 | 2.6 | 512.7 |
| 26 | 32.6 | 14.5 | 67.2 | 6.4 | 124.1 | 87.6 | 9.7 | 94.4 | 10.3 | 2.3 | 9.7 | 2.3 | 461.1 |
| 29 | 29.3 | 13.5 | 57.7 | 6.4 | 114.0 | 81.6 | 9.4 | 89.5 | 10.6 | 1.9 | 11.0 | 2.0 | 426.7 |
| 39 | 32.2 | 13.7 | 72.8 | 6.3 | 129.3 | 82.0 | 8.9 | 100.2 | 9.7 | 2.3 | 10.3 | 2.1 | 469.7 |
| 42 | 24.4 | 11.7 | 58.6 | 5.2 | 123.0 | 83.0 | 11.8 | 103.6 | 11.8 | 2.6 | 17.4 | 3.3 | 456.2 |
| 52 | 33.4 | 15.1 | 78.3 | 6.5 | 116.9 | 57.8 | 11.2 | 110.0 | 9.0 | 2.5 | 12.6 | 3.0 | 456.2 |
| 54 | 33.0 | 14.0 | 73.1 | 6.8 | 131.3 | 91.2 | 10.1 | 119.5 | 11.5 | 3.0 | 11.6 | 1.3 | 506.3 | tr* = trace; <0.2 wt %

In certain of these SLC1-1 $T_2$ lines, the proportion of VLCFA-containing TAGs (e.g. in Tables 3 and 4), and hence, seed content of total VLCFAs, especially eicosenoic acid and erucic acid, were dramatically increased (Table 5). In some cases, the overall proportions of VLCFAs were also increased (Table 6).

Those SLC1-1 transformed $T_2$ lines showing the most promising results in terms of increased oil content and increased proportions of VLCFA-containing TAGs, were selected and individual seeds planted to give $T_3$ progeny lines. Lipid analyses of TAGs from several independent SLC1-1 transgenic $T_3$ lines indicated that there was significantly increased total lipid content (reported as μg fatty acids/100 seeds; Table 7) which correlated with increased TAG content (nmol TAG/100 seeds; Table 8), compared to pBI121 Control $T_3$ transformants. In particular, the amounts of VLCFAs (μg/100 seeds; Table 7) and levels of VLCFA-containing $C_{58}$ and $C_{60}$ TAGs (Table 8), were greatly enhanced in several SLC1-1 transformants, over pBI121 control plants.

Stereospecific analyses of TAGs from selected independent $T_3$ SLC1-1 transgenics contained increased proportions of VLCFAs (e.g. eicosenoic acid, 20:1) at the sn-2 position. This trend was consistent, regardless of whether the data was expressed as the proportion, among all sn-2 position fatty acids, which is represented by eicosenoic acid, or as the proportion of total eicosenoic acid in TAGs which is found at the sn-2 position (Table 9). Furthermore, in the SLC1-1 transgenics, the increase in proportions of VLCFAs (e.g. eicosenoic acid) at the sn-2 position of TAGs was correlated with a concomitant decrease in the proportions of polyunsaturated fatty acids at this position, in comparison to pBI121 control plants (FIG. 4).

TABLE 3

TAG Species Accumulating in $T_2$ Seeds of Untransformed WT Control
*A. thaliana*, and SLC1-1 Transformant #42 (nmol/50 seeds ± SD)

| Line | TAG C#→ | $C_{50}$ | $C_{52}$ | $C_{54}$ | $C_{56}$ | $C_{58}$ | $C_{60}$ | Total |
|---|---|---|---|---|---|---|---|---|
| WT Con | nmol ± | 5.9 | 44.3 | 115.3 | 163.3 | 56.9 | 5.9 | 391.6 |
| (n = 5) | SD | 0.3 | 3.2 | 10.3 | 16.3 | 7.3 | 1.4 | 37.3 |
|  | mol % ± | 1.5 | 11.3 | 29.5 | 41.7 | 14.5 | 1.5 | 100.0 |
|  | SD | 0.1 | 0.4 | 0.7 | 0.4 | 0.8 | 0.3 |  |
|  | mol % $C_{56}$-$C_{60}$ | 57.7 |  |  |  |  |  |  |
| 42 | nmol ± | 3.5 | 32.7 | 108.1 | 194.3 | 95.6 | 16.6 | 450.8 |
| (n = 2) | SD | 0.1 | 0.2 | 0.9 | 0.4 | 1.2 | 0.8 | 3.5 |
|  | mol % ± | 0.8 | 7.2 | 24.0 | 43.1 | 21.2 | 3.7 | 100.0 |
|  | SD | 0.01 | 0.01 | 0.004 | 0.3 | 0.1 | 0.2 |  |
|  | mol % $C_{56}$-$C_{60}$ | 68.0 |  |  |  |  |  |  |

TABLE 4

TAG Species Accumulating in $T_2$ Seeds of Untransformed WT Control *A. thaliana*, and
SLC1-1 Transformant #16 (nmol/50 seeds ± SD)

| WT Con | nmol | 5.9 | 44.3 | 115.3 | 163.3 | 56.9 | 5.9 | 391.6 |
|---|---|---|---|---|---|---|---|---|
| (n = 5) | SD | 0.3 | 3.2 | 10.3 | 16.3 | 7.3 | 1.4 | 37.3 |
|  | mol % | 1.5 | 11.3 | 29.5 | 41.7 | 14.5 | 1.5 | 100.0 |
|  | SD | 0.1 | 0.4 | 0.7 | 0.4 | 0.8 | 0.3 |  |
|  | mol % $C_{56}$-$C_{60}$ | 57.7 |  |  |  |  |  |  |
| 16 | nmol | 6.5 | 51.3 | 144.1 | 214.9 | 82.7 | 10.6 | 510.1 |
| (n = 2) | SD | 0.1 | 0.3 | 1.4 | 2.9 | 2.0 | 0.6 | 7.1 |
|  | mol % | 1.3 | 10.1 | 28.3 | 42.1 | 16.2 | 2.1 | 100.0 |
|  | SD | 0.04 | 0.1 | 0.1 | 0.02 | 0.2 | 0.1 |  |
|  | mol % $C_{56}$-$C_{60}$ | 60.4 |  |  |  |  |  |  |

TABLE 5

Eicosenoic (20:1), Eurcic (22:1) and Total Very-Long Chain
Fatty Acid (VLCFA) Content of $T_2$ Seed In Untransformed
WT Control *A. thaliana*, pBI121 Controls and SLC1-1
Transgenic Lines (μg/50 seeds)

| Line | 20:1 | 22:1 | Total VLCFAs |
|---|---|---|---|
| WT Con | 74.8 | 8.3 | 102.8 |
| SD (n = 5) | 6.4 | 0.7 | 10.1 |
| pBI121 Con | 73.8 | 7.0 | 96.7 |
| SD (n = 2) | 2.3 | 0.3 | 3.4 |
| 16 | 96.4 | 11.0 | 132.6 |
| 20 | 118.8 | 12.4 | 159.2 |
| 23 | 106.9 | 11.7 | 146.4 |
| 42 | 103.6 | 17.4 | 150.3 |
| 52 | 110.0 | 12.6 | 148.2 |
| 54 | 119.5 | 11.6 | 156.8 |

TABLE 6

Proportions of Eicosenoic Acid (20:1), and Total VLCFAs
in $T_2$ Seed of Untransformed WT Controls (u-WT),
pBI121 Controls, and Selected SLC1-1 Transgenic Lines of
*A. thaliana* (wt % in 50-seed samples)

| Line | 20:1 | All VLCFAs |
|---|---|---|
| u-WT Con | 20.0 | 27.6 |
| pBI121 Con | 20.5 | 26.3 |

TABLE 6-continued

Proportions of Eicosenoic Acid (20:1), and Total VLCFAs
in $T_2$ Seed of Untransformed WT Controls (u-WT),
pBI121 Controls, and Selected SLC1-1 Transgenic Lines of
*A. thaliana* (wt % in 50-seed samples)

| Line | 20:1 | All VLCFAs |
|---|---|---|
| 42 | 22.7 | 33.0 |
| 52 | 24.1 | 32.5 |
| 54 | 23.6 | 31.0 |

TABLE 7

Total Lipid Content (μg total FA/100 seeds) and VLCFA Content (μg/100 seeds) in Mature $T_3$ Seed of pBI121 Controls (pBI121 Con), and Selected SLC1-1 Transgenic Lines of A. thaliana (μg/100 seeds)

| Line | Total Lipid Content | VLCFA Content |
|---|---|---|
| pBI121 Con a | 483.5 | 119.7 |
| pBI121 Con b | 568.5 | 127.2 |
| pBI121 Con c | 519.7 | 125.1 |
| pBI121 Con d | 511.3 | 122.3 |
| pBI121 Con Avg ± | 520.7 | 123.6 |
| SE (n = 4) | 15.3 | 1.4 |
| 42-1 | 1137.9 | 315.5 |
| 42-4 | 851.7 | 218.6 |
| 42-5 | 984.6 | 268.0 |
| 23-8 | 1056.1 | 287.7 |
| 52-2 | 1109.2 | 307.5 |
| 52-5 | 870.0 | 253.3 |
| 52-6 | 1039.1 | 231.6 |
| 16-5 | 1955.3 | 227.0 |

TABLE 8

Total TAG Content and $C_{58}$ and $C_{60}$ TAG Content of Mature $T_3$ Seed of pBI121 Controls (pBI121 Con), and Selected SLC1-1 Transgenic Lines of A. thaliana (nmol/100-seed samples)

| TAG C #→ | $C_{50}$ | $C_{52}$ | $C_{54}$ | $C_{56}$ | $C_{58}$ | $C_{60}$ | Total |
|---|---|---|---|---|---|---|---|
| pBI121 Con ± | 8.5 | 55.3 | 130.9 | 145.3 | 30.9 | nd* | 371.0 |
| SE (n = 6) | 0.4 | 2.6 | 7.8 | 9.0 | 2.7 | | 21.6 |
| 16-5 | 12.4 | 88.2 | 214.7 | 251.6 | 70.5 | 5.6 | 642.9 |
| 23-8 | 17.7 | 130.8 | 333.6 | 409.0 | 106.8 | 8.0 | 1005.9 |
| 42-4 | 11.4 | 90.7 | 259.6 | 366.4 | 127.7 | 14.3 | 870.0 |
| 52-6 | 15.2 | 106.1 | 252.1 | 322.7 | 85.5 | 6.0 | 787.7 |

\* nd = not detected

TABLE 9

Proportion of 20:1 at the sn-2 Position of TAGs (wt % sn-2 20:1) and Proportion of Total 20:1 Found at the sn-2 Position of TAGs (wt % of total 20:1 at sn-2 position) in Mature $T_3$ Seed of pBI121 Controls (pBI121 Con), and Selected SLC1-1 Transgenic Lines of A. thaliana (wt %/100-seed samples)

| Line | wt % sn-2 20:1 | wt % of Total 20:1 at sn-2 position * |
|---|---|---|
| pBI121 Con a | 1.7 | 3.6 |
| pBI121 Con b | 0.6 | 1.1 |
| pBI121 Con c | 0.5 | 0.9 |
| pBI121 Con d | 1.6 | 3.0 |
| 16-5 | 4.2 | 16.3 |
| 42-1 | 5.1 | 8.5 |
| 42-4 | 7.9 | 12.8 |
| 42-5 | 5.3 | 8.7 |
| 23-8 | 7.5 | 12.0 |
| 52-2 | 6.2 | 10.0 |
| 52-5 | 5.8 | 9.7 |
| 52-6 | 7.5 | 12.0 |

\* % of Total 20:1 in sn-2 position = (% in [sn-2/[3 × % Total 20:1]] × 100)

B. napus and B. carinata SLC1-1 Transformant Seed Lipid Analyses:

Several B. napus cv. Hero, cv. Reston, and B. carinata SLC1-1 $T_2$ transformant seed lines exhibited increased oil content (Table 10) and increased erucic acid content, expressed as μg/mg DW, or as μg/seed (Table 11). In B. napus cvs. Hero and Reston, seeds of several SLC1-1 transgenic lines exhibited increased proportions of erucic acid (Table 12), compared to the corresponding levels in untransformed control plants. Single seed analyses from a selected average untransformed Hero plant (plant 4) and an SLC1-1 transformant line with a promising high oil yield and high erucic acid phenotype (Line 8, plant 6) indicated a distribution of these traits suggestive of a seed population segregating in a typical Mendelian fashion for a single insert (Table 13). Some seeds of Hero Line 8 plant 6, exhibited probable homozygous WT (e.g. seed 8-6I) or homozygous SLC1-1 (e.g. seeds 8-6K and 8-6H) phenotypes for all three traits (high oil yield, increased erucic acid content, increased proportions of erucic acid), while others displayed probable heterozygous WT/SLC1-1 profiles with intermediate values for these three traits (e.g. seed 8-6B).

TABLE 10

Oil Yield (% Dry Weight) in $T_2$ Seeds of Untransformed Control (Con) and Selected SLC1-1 Transgenic Lines of B. napus cvs. HERO and RESTON, and in B. carinala breeding line C90-1163 (± SE where applicable).

| Line | Oil Yield (% DW) |
|---|---|
| B. napus cv HERO | |
| Con | 40.1 ± 1.7 |
| 5-1 | 46.7 |
| 5-4 | 48.7 |
| 7-3 | 45.3 |
| 7-6 | 46.4 |
| 7-9 | 44.9 |
| 8-4 | 45.9 |
| 8-6 | 50.9 |
| 8-7 | 44.9 |
| 8-10 | 45.1 |
| B. napus cv RESTON | |
| Con | 33.4 ± 2.2 |
| 1-7 | 41.9 |
| 1-8 | 40.5 |
| 2-8 | 42.1 |
| 2-9 | 42.2 |
| Brassica carinata line C90-1163 | |
| Con | 35.9 ± 1.1 |
| B. car 10-1-7 | 42.8 |
| B. car 2-3-6 | 39.9 |

TABLE 11

Erucic Acid Content (expressed as μg/mg DW or μg/seed) in Mature $T_2$ Seeds of Untransformed Control (Con) and Selected SLC1-1 Transgenic Lines of B. napus cv. HERO, and in B. carinata breeding line C90-1163 (± SE for Controls).

| Line | 22:1 (μg/mg DW) | 22:1 (μg/seed) |
|---|---|---|
| Brassica carinata line C90-1163 | | |
| Con | 156.4 ± 5.6 | -- |
| 10-1-7 | 180.4 | -- |
| B. napus cv HERO | | |
| Con | 195.5 ± 11.7 | 596.7 ± 40.8 |
| 5-1 | 247.9 | 900.6 |
| 5-4 | 247.4 | 818.8 |
| 7-3 | 236.1 | -- |
| 7-6 | 244.8 | 912 |
| 7-9 | 229.2 | 857.6 |
| 8-4 | 235.7 | 923.2 |
| 8-6 | 270.9 | 1020.3 |
| 8-7 | 238.5 | 888.3 |
| 8-10 | 232.7 | 900.4 |
| 3-1 | -- | -- |

-- not determined

TABLE 12

Proportions of Erucic Acid (expressed as wt %) in Mature $T_2$
Seeds of Untransformed Control (Con) and Selected SLC1-1
Transgenic Lines of *B. napus* cvs. HERO and
RESTON (± SE for Controls).

| Line | wt % 22:1 |
|---|---|
| *B. napus* cv HERO | |
| Con | 48.6 ± 0.6 |
| 5-1 | 53.1 |
| 5-4 | -- |
| 7-3 | 52.1 |
| 7-6 | 52.8 |
| 7-9 | -- |
| 8-4 | 51.4 |
| 8-5 | 53.3 |
| 8-7 | 51.8 |
| 8-10 | 53.6 |
| 3-1 | 58.3 |
| *B. napus* cv RESTON | |
| Con | 34.7 ± 0.2 |
| 1-10 | 36.4 |
| 1-7 | 35.8 |
| 1-8 | 37.4 |
| 2-3 | 36.6 |
| 2-7 | 41.1 |

-- not determined

TABLE 13

Variation in Lipid Content (expressed as μg total fatty acids/seed)
and Erucic Acid Content (expressed as μg 22:1/seed or as wt % 22:1)
in Mature $T_2$ Single Seeds of Untransformed Control plant 4
and SLC1-1 Transgenic Line-8 plant 6 of *B. napus* cv. HERO
(± SE for Averages, AVG).

| Line/Seed | μg FAs/seed | μg 22:1/seed | Wt % 22:1 |
|---|---|---|---|
| AVG Con 4 | 1076.7 ± 61.5 | 507.1 ± 33.7 | 46.9 ± 0.8 |
| AVG-8 6 | 1441.7 ± 67.3 | 735.4 ± 36.5 | 51.0 ± 0.6 |
| 8 6G | 1324.8 | 710.8 | 54.1 |
| 8 6H | 1704.3 | 877.1 | 52.5 |
| 8 6I | 1175.4 | 557.3 | 47.4 |
| 8 6J | 1206.8 | 629.4 | 52.2 |
| 8 6K | 1694.7 | 911.1 | 53.8 |
| 8 6A | 1351.6 | 658.6 | 48.7 |
| 8 6B | 1304.5 | 670.6 | 51.4 |
| 8 6C | 1221.1 | 639.1 | 52.3 |
| 8 6D | 1449.0 | 714.3 | 49.3 |
| 8 6E | 1678.2 | 844.6 | 50.3 |
| 8 6F | 1748.0 | 876.8 | 50.2 |

There were measurable increases in the proportions of erucic acid and total VLCFAs at the sn-2 position in several transformant lines of Hero (Table 14). The effect of the yeast transgene on increasing the sn-2 erucic acid content in *B. napus* was somewhat less dramatic than its ability to change the sn-2 eicosenoic acid content in *A. thaliana* (c.f. Table 9). However, this is perhaps, not unexpected, based on the relative specificity of the *S. cerevisiae* sn-2 acyltransferase for eicosenoyl- vs erucoyl-CoA (c.f. Table 1).

TABLE 14 sn-2 Erucic Acid and VLCFA Content in Mature $T_2$ Seeds of
Untransformed Control and Selected SLC1-1 Transgenic Lines of
*B. napus* cv. HERO.

| Line/Seed | sn-2 22:1 | sn-2 VLCFAs |
|---|---|---|
| Hero Control | 1.5 | 3 |
| Hero 8-6 | 2.8 | 4.6 |
| Hero 8-6 G (single seed) | 3.6 | 4.44 |
| Hero 3-1 | 4.12 | 4.12* |
| Hero 8-10 | 2.22 | 3.7 |

*Erucic acid (22:1) is the only sn-2 VLCFA detected.

Analyses of TAG species composition by GC, indicated that several SLC1-1 transformant lines of Hero had increased proportions of $C_{62}$ TAGs, and to a lesser extent, $C_{64}$ and $C_{66}$ TAGs (Table 15). The proportions of $C_{62}$–$C_{66}$ TAGs containing 2 or more $C_{22}$ fatty acids, was dramatically increased in Hero SLC1-1 transgenics (Table 15), primarily at the expense of TAGs containing two ($C_{56}$) or three ($C_{54}$) $C_{10}$ fatty acids (data not shown). A similar increase in the proportion of $C_{62}$ TAGs was observed in some *B. napus* cv. Reston SLC1-1 transgenic lines (Table 15).

TABLE 15

Proportions of $C_{62}$, $C_{64}$ and $C_{66}$ TAGs (mol %) in Mature
$T_2$ Seed of Untransformed Control (Con) and Selected SLC1-1
Transgenic Lines of *B. napus* cvs. HERO and RESTON
(± SE for Controls).

| Line | $C_{62}$ | $C_{64}$ | $C_{66}$ | Total $C_{62}$-$C_{66}$ |
|---|---|---|---|---|
| Control | 36.72 ± 1.42 | 1.32 ± 0.02 | 0.10 ± 0.01 | 38.14 ± 1.45 |
| Hero 5-2 | 51.44 | 1.61 | 0.12 | 53.37 |
| Hero 5-4 | 48.92 | 1.95 | 0.25 | 51.12 |
| Hero 5-10 | 56.48 | 1.45 | 0.08 | 58.02 |
| Hero 7-1 | 57.25 | 2.19 | 0.14 | 59.56 |
| Hero 7-5 | 55.61 | 1.98 | 0.09 | 57.68 |
| Hero 8-4 | 44.76 | 2.14 | 0.25 | 47.16 |
| Hero 8-8 | 53.35 | 2.22 | 0.22 | 55.79 |
| Reston | | | | |
| Control | 18.32 | 0.94 | 0.06 | 19.32 |
| 1-5 | 23.88 | 1.06 | 0.07 | 25.01 |
| 2-7 | 31.57 | 1.42 | 0.11 | 33.20 |

Analyses of typical control and SLC1-1 *B. napus* cv. Hero transgenics with respect to the seed-to-seed variation in proportions of $C_{62}$ TAGs, indicated that the SLC1-1 $T_2$ seed population was segregating, but that many of the single seeds had considerably higher proportions of $C_{62}$ TAGs than any of the untransformed controls (Table 16).

TABLE 16

Single Seed Analyses for Proportions of $C_{62}$ TAGs (mol %) in Mature
$T_2$ Seeds of Untransformed Control (Con) and SLC1-1
Transgenic Lines of *B. napus* cv. HERO (± SE
for averages, AVG).

| Line/Seed | $C_{62}$ TAGs |
|---|---|
| Hero Con | |
| 4d | 38.54 |
| 4e | 40.29 |

TABLE 16-continued

Single Seed Analyses for Proportions of $C_{62}$ TAGs (mol %) in Mature $T_2$ Seeds of Untransformed Control (Con) and SLC1-1 Transgenic Lines of *B. napus* cv. HERO (± SE for averages, AVG).

| Line/Seed | $C_{62}$ TAGs |
|---|---|
| 4b | 36.88 |
| 4f | 38.81 |
| 4g | 30.05 |
| 4j | 35.95 |
| 4h | 42.84 |
| 4l | 40.81 |
| 4k | 43.28 |
| Hero Con AVG | 38.6 ± 1.35 |
| Hero 8-6 | |
| 8-6d | 36.36 |
| 8-6a | 47.63 |
| 8-6b | 54.06 |
| 8-6c | 54.81 |
| 8-6f | 44.4 |
| 8-6g | 56.27 |
| 8-6h | 53.11 |
| 8-6l | 42.19 |
| 8-6j | 51.44 |
| 8-6k | 58.4 |
| Hero 8-6 AVG | 51.35 ± 1.82 |

TABLE 17

$^1$H-NMR Integral Response for Resonances Assigned to Liquidlike Oil (as described by Rutar; 1989) in Mature $T_2$ Seeds of Untransformed Controls and Selected SLC1-1 Transgenic Lines of *B. napus* cv. HERO and *B. carinata* breeding line C90-1163. (35-seed samples; Responses relative to Control integration, set at 1,000)

| Line | NMR Integral Response |
|---|---|
| *B. napus* cv HERO | |
| Control | 1.0000 |
| Hero 5-1 | 1.5175 |
| Hero 7-3 | 1.2721 |
| Hero 7-6 | 1.3875 |
| Hero 7-9 | 1.3245 |
| Hero 8-4 | 1.5667 |
| Hero 8-6 | 1.5297 |
| Hero 8-7 | 1.4825 |
| Hero 8-10 | 1.6302 |
| *B. carinata* cv. C90-1163 | |
| Control | 1.0000 |
| *B. car.* 10-1-7 | 1.5977 |
| *B. car.* 2-3-6 | 1.7548 |

Estimates of oil yield increases in SLC1-1 transgenic lines relative to controls, were directly correlated whether expressed on a "per mg dry weight" basis or on a "per seed" basis (FIG. 5), as were estimates of relative oil content by a non-destructive $^1$H-NMR method (FIG. 6). Indeed, the NMR results for increased oil yield were also positively correlated with increased seed weights in the SLC1-1 transgenics (FIG. 7), and indicated that contributions to increased seed dry weight were directly attributable to increased oil, with negligible contribution from seed water (absence of broad water resonance between the $CH_2$ OCO— and CHOCO— chemical shifts). Typical $^1$H-NMR responses from 35-seed samples of control and "high oil" SLC1-1 transgenic lines of *B. napus* cv. Hero and *B. carinata*, are depicted in Table 17.

Some *B. napus* cv Westar (Canola) SLC1-1 $T_2$ transformant seed lines showed increases in the relative proportion of oleic acid, and concomitant decreases in the relative proportions of polyunsaturated fatty acids (18:2 and 18:3) (Table 18). This is in contrast to the predicted effect as cited in the University of Kentucky patent application. Thus, the proportions of mono-unsaturated fatty acids can be increased in edible oils, by expression of SLC1-1. Furthermore, the proportions of saturated very long chain fatty acids in these Canola lines were significantly increased (Table 18).

TABLE 18

Oleic, Linoleic, Linolenic and Saturated VLCFA Compositions of Untransformed Control and Selected SLC1-1 Transgenic Lines of *B. napus* cv. WESTAR (n = 2 or 3)

| Line | Oleic 18:1c9 | Linoleic 18:2 c9,12 | Linolenic 18:3 c9,12,15 | Eicosanoic 20:0 | Behenic 22:0 | Lignoceric 24:0 |
|---|---|---|---|---|---|---|
| *B. napus* cv WESTAR | | | | | | |
| Control | 61.03 | 17.55 | 11.07 | 0.55 | 0.31 | 0.27 |
| WS-13 | 70.03 | 14.80 | 3.41 | 0.76 | 0.49 | 0.56 |

TABLE 18-continued

Oleic, Linoleic, Linolenic and Saturated VLCFA Compositions of Untransformed
Control and Selected SLC1-1 Transgenic Lines of *B. napus* cv. WESTAR
(n = 2 or 3)

| Line | Oleic 18:1c9 | Linoleic 18:2 c9,12 | Linolenic 18:3 c9,12,15 | Eicosanoic 20:0 | Behenic 22:0 | Lignoceric 24:0 |
|---|---|---|---|---|---|---|
| WS-15 | 71.92 | 12.33 | 3.71 | 0.78 | 0.53 | 0.48 |
| WS-16 | 71.06 | 12.29 | 3.87 | 0.97 | 0.59 | 0.56 |
| WS-15a | 72.71 | 9.69 | 3.09 | 0.94 | 0.65 | 0.68 |

LPAT Analyses of Transformant Lines:

Samples of *B. napus* cv. Westar and *B. napus* cv. Argentine SLC1-1 $T_1$ transformant lines exhibited increased leaf 18:1-CoA:LPAT activities in rapidly-expanding leaf homogenate preparations compared to those from untransformed control plants (Table 19).

Developing seed LPAT analyses in untransformed control and SLC1-1 transgenics of *B. napus* cv. Hero and *B. carinata* indicated that both 18:1-CoA:LPAT and 22:1-CoA:LPAT (Table 19) specific activities were dramatically increased in the SLC1-1 transgenics.

Developing seed LPAT analyses of untransformed control and SLC1-1 transgenics of *A. thaliana* indicated that 20:1-CoA:LPAT activity was increased in several SLC1-1 transgenics (Table 19).

Thus, in this deposition we provide, for the first time, direct evidence that the yeast SLC1-1 gene product encodes an enzyme which possesses sn-2 acyltransferase activity, and which can exhibit LPAT (EC 2.3.1.51) activity in vitro.

TABLE 19

Relative LPAT Activities in Homogenates Prepared from $T_1$ Leaf and
$T_2$ or $T_3$ Developing Seed of Untransformed Controls and
Selected SLC1-1 Transgenic Lines of *B. napus* cvs. WESTAR,
ARGENTINE and HERO, *B. carinata* cv. C90-1163, and *A. thaliana*
cv. COLUMBIA. All assays conducted as described in
experimental section.

| Line | Tissue Assayed | LPAT Activity Assayed | DPM $^{14}$C acyl-CoA incorporated into PA/µg pr |
|---|---|---|---|
| *B. napus* Westar Control | $T_1$ Leaves | 18:1-CoA | 307 |
| WS 2-5 | | | 1008 |
| WS 3-8 | | | 617 |
| WS 6-7 | | | 1428 |
| *B. napus* Arg. Control | $T_1$ Leaves | 18:1-CoA | 350 |
| Arg 2-8 | | | 996 |
| Arg 3-3 | | | 1557 |
| *B. napus* Hero Control | $T_2$ Dev. Seeds | 18:1-CoA | 580 |
| Hero 3-1 | | | 3470 |
| Hero 7-6 | | | 2035 |
| Hero 8-6 | | | 1370 |
| *B. car.* C90-1163 Control | $T_2$ Dev. Seed | 18:1-CoA | 720 |
| *B. car* 10-1-7 | | | 1125 |
| *B. napus* Hero Control | $T_2$ Dev. Seeds | 22:1-CoA | 6.4 |
| Hero 3-1 | | | 68.3 |
| Hero 7-6 | | | 53.4 |
| Hero 8-6 | | | 20.2 |

TABLE 19-continued

Relative LPAT Activities in Homogenates Prepared from $T_1$ Leaf and
$T_2$ or $T_3$ Developing Seed of Untransformed Controls and
Selected SLC1-1 Transgenic Lines of *B. napus* cvs. WESTAR,
ARGENTINE and HERO, *B. carinata* cv. C90-1163, and *A. thaliana*
cv. COLUMBIA. All assays conducted as described in
experimental section.

| Line | Tissue Assayed | LPAT Activity Assayed | DPM $^{14}$C acyl-CoA incorporated into PA/µg pr |
|---|---|---|---|
| *A. thaliana* WT u-Control | $T_3$ Dev. Seeds | 20:1-CoA | 238 |
| 42-1 | | | 270 |
| 42-4 | | | 380 |
| 42-5 | | | 503 |

Genetic Analyses of SLC1-1 Transformants:
PCR and Southern analyses data for the transgenic plant lines cited in this deposition are summarized in Table 20.

TABLE 20

Summary of PCR and Southern data
for SLC1-1 $T_2$ transgenic plant lines (nd = not determined)

| Oilseed | Transformant # ($T_2$ line) | PCR | Southern | Insert (Copy) # |
|---|---|---|---|---|
| *A. thaliana* cv. COLUMBIA | 16 | + | + | single |
| | 20 | + | + | single |
| | 23 | + | + | multiple |
| | 42 | + | + | multiple |
| | 52 | + | + | multiple |
| | 54 | + | + | multiple |
| *B. napus* cv. WESTAR | 2 | + | + | multiple |
| | 3 | + | + | multiple |
| | 6 | + | + | multiple |
| | 13 | nd | + | single |
| | 15 | nd | + | multiple |
| | 16 | nd | + | multiple |
| *B. napus* cv. ARGENTINE | 2 | + | + | multiple |
| | 3 | + | + | multiple |
| *B. napus* cv. HERO | 5 | + | + | single |
| | 7 | + | + | single |
| | 8 | + | + | single |
| | 3 | + | + | single |
| *B. carinata* cv. C90-1163 | 10 | + | + | single |
| | 2 | + | + | multiple |

To follow the segregation pattern in the $T_2$ generation of *A. thaliana* SLC1-1 transformants, seeds from transgenic lines (e.g. lines 16, 20) which showed increases in oil content and amounts of long ($C_{18}$) and very long chain fatty acids ($C_{20}$ and $C_{22}$) were sterilized and germinated on selective medium(50 mg/L kanamycin). Both lines showed the same 3:1 (kanamycin resistant:kanamycin sensitive) segregation pattern which indicates that the marker segregates as one Mendelian locus. Southern hybridization analyses (Southern, 1975) confirmed the presence of a single T-DNA insert per genome. In lines 23, 42, 52 and 54, Southern hybridization analyses suggest that all of the lines have more than one T-DNA insert per genome.

Northern hybridization analyses of seeds at mid-development isolated from siliques of *A. thaliana* lines 16, 20, 23, 42, 52 and 54 confirmed the expression of SLC1-1 gene in all lines tested, with the highest level of expression in line 42.

Southern analysis of genomic DNA which was isolated from *B. napus* cv. Westar transgenic lines (2, 3, 6, 13, 15, 16) revealed that only line 13 had a single insert. Both *B. napus* cv. Argentine SLC1-1 transgenic lines (2, 3) had multiple inserts. *B. napus* cv. Hero transgenic lines (3, 5, 7, 8) and *B. carinata* transgenic line 10, each had a single insert, while *B. carinata* line 2 had multiple T-DNA inserts per genome.

References of Interest to the Present Invention

1. Alexander, D. E., Silvela, L. S., Collins, F. I. and Rodgers, R. C. (1967) Analysis of oil content of maize by wide-line NMR. *J. Am. Oil Chem. Soc.* 44: 555–558.
2. Ausubel, F. M., Brent, R., Kingston, R. E., Moore, D. D., Seidman, J. G., Smith, J. A. and Stuhl, K. (1995) *Current Protocols in Molecular Biology*, Vols 1, 2 and 3.
3. Bechtold, N., Ellis, J., and Pelletier, G. (1993) In planta *Agrobacterium*-mediated gene transfer by infiltration of adult *Arabidopsis thaliana* plants. *C R Acad Sci Paris, Sciences de la vie/Life sciences* 316: 1194–1199.
4. Brown, A. P., Coleman, J., Tommey, A. M., Watson, M. D., and Slabas, A. R. (1994) Isolation and characterization of a maize cDNA that complements a 1-acyl-sn-glycerol-3-phosphate acyltransferase mutant of *Escherichia coli* and encodes a protein which has similarities to other acyltransferases. *Plant Mol. Biol.* 26: 211–223.
5. Brown, A. P., Brough, C. L., Kroon, J. T. M. and Slabas, A. R. (1995) Identification of a cDNA that encodes a 1-acyl-sn-glycerol-3-phosphate acyltransferase from *Limnanthes douglasii*. *Plant Mol. Biol.* 29: 267–278.
6. Coleman, J. (1990) Characterization of *Escherichia coli* cells deficient in 1-acyl-sn-glycerol-3-phosphate acyltransferase activity. *J. Biol. Chem.* 265: 17215–17221.
7. Coleman, J. (1992) Characterization of the *Escherichia coli* gene for 1-acyl-sn-glycerol-3-phosphate acyltransferase (plsC). *Mol. Gen. Genet.* 232: 295–303.
8. Datla, R., Hammerlindl, J. K., Panchuk, B., Pelcher, L. E. and Keller, W. A. (1992) Modified binary plant transformation vectors with the wild-type gene encoding NPTII. *Gene*, 211: 383–384.
9. Datla, R. S. S., Bekkaoui, F., Hammerlindl, J., Pilate, G., Dunstan, D. I. and Crosby, W. L. (1993) Improved high-level constitutive foreign gene expression in plants using an AMV RNA4 untranslated leader sequence. *Plant Science*, 94:139–149.
10. De Lange, P., Van Blokland, R., Kooter, J. M., and Mol, J N. M. (1995) Suppression of flavenoid flower pigmentation genes in *Petunia hybrida* by the introduction of anti-sense and sense genes. In: Meyer, P. (ed) *Gene silencing in higher plants and related phenomena in other eukaryotes.* Springer-Verlag, Berlin pp. 57–75.
11. DeBlock, M., DeBrouwer, D., and Tenning, P. (1989) Transformation of *Brassica napus* and *Brassica oleracea* using *Agrobacterium tumefaciens* and the expression of the bar and neo genes in the transgenic plants, *Plant Physiol.* 91: 694–701.
12. Hitz, W. D., Mauvis, C. J., Ripp, K. G., Reiter, R. J., DeBonte, L. and Chen, Z. (1995) The use of cloned rapeseed genes for cytoplastic fatty acid desaturases and the plastid acyl-ACP thioesterases to alter relative levels of polyunsaturated and saturated fatty acids in rapeseed oil. *Proc. 9th Internat'nal Cambridge Rapeseed Congress UK,* pp. 470–472.
13. Jefferson, R. A., Kavanagh, T. A. and Bevan, M. W. (1987) GUS fusions: β-glucuronidase as a sensitive and versatile gene fusion marker in higher plants. *EMBO J.,* 6: 3901–3907.
14. Katavic V., Haughn, G. W., Reed, D., Martin, M., and Kunst L. (1994). In planta transformation of *Arabidopsis thaliana. Mol. Gen. Genet.* 245: 363–370.
15. Katavic, V., Reed, D. W., Taylor, D. C., Giblin, E. M., Barton, D. L., Zou, J- T., MacKenzie, S. L., Covello, P. S. and Kunst, L. (1995). Alteration of Fatty Acid Composition by an EMS-Induced Mutation in *Arabidopsis thaliana* Affecting Diacylglycerol Acyltransferase Activity. *Plant Physiol.* 108:399–409.
16. Knutzon, D. S., Thompson, G. A., Radke, S. E., Johnson, W. B., Knauf, V. C., and Kridl, J. C. (1992) Modification of Brassica seed oil by anti-sense expression of a stearoyl-acyl carrier protein desaturase gene. *Proc. Nat'l Acad. Sci. USA,* 89: 2624–2628.
17. Knutzon, D. S., Lardizabal, K. D., Nelson J. S., Bleibaum, J. L., Davies, H. M. and Metz, J. (1995a) Cloning of a coconut endosperm cDNA encoding a 1-acyl-sn-glycerol-3-phosphate acyltransferase that accepts medium chain length substrates. *Plant Physiol.* 109: 999–1006.
18. Knutzon, D. S., Lardizabal, K. D., Nelson J. S., Bleibaum, J. L., and Metz, J. (1995b) Molecular cloning of a medium chain-preferring lyso-phosphatidic acid acyltransferase from immature coconut endosperm. *2nd NPLC Symposium on the Biochemistry and Molecular Biology of Plant Fatty Acids and Glycerolipids,* Lake Tahoe, Calif.; Abstr. P-211.
19. Koncz, C. and Schell, J. (1986) The promoter of $T_1$-DNA gene 5 controls the tissue-specific expression of chemaeric genes by a novel type of Agrobacterium binary vector. *Mol. Gen. Genet.* 204: 383–396.
20. Lassner, M. W., Lardizabal, K, and Metz, J. G. (1996) A jojoba β-ketoacyl-CoA synthase cDNA complements the canola fatty acid elongation mutation in transgenic plants. *The Plant Cell,* 8: 281–292.
21. Lassner, M. W., Levering, C. K., Davies, H. M., and Knutzon, D. S. (1995) Lysophosphatidic acid acyltransferase from meadowfoam mediates insertion of erucic acid at the sn-2 position of triacylglycerol in transgenic rapeseed oil. *Plant Physiol.* 109: 1389–1394.
22. Lester, R. L., Wells, G. B., Oxford, G. and Dickson, R. C. (1993) Mutant strains of *Saccharomyces cerevisiae* lacking sphingolipids synthesize novel inositol glycerolipids that mimic sphingolipid structures. *J. Biol. Chem.* 268: 845–856.
23. Mol, J. N. M., Van der Krol, A. R., Van Tunen, A. J., Van Blokland, R., De Lange, P., and Stuitje, A. R. (1990) Regulation of plant gene expression by antisense RNA. *FEBS Lett.* 268: 427–430.
24. Moloney, M. M., Walker, J. M. and Sharma, K. K. (1989) High efficiency transformation of *Brassica napus* using Agrobacterium vectors. *Plant Cell Reports,* 2438–2442.
25. Nagiec, M. M., Wells, G. B., Lester, R. L., and Dickson, R. C. (1993) A suppressor gene that enables *Saccharomyces cerevisiae* to grow without making sphingolipids encodes a protein that resembles in *Escherichia coli* fatty acyltransferase. *J. Biol. Chem.* 268: 22156–22163.
26. Roscoe, T., Delseny, M., Lessire, R. and Renard, M. (1995) Modification of triacylglycerol composition. *2nd NPLC Symposium on the Biochemistry and Molecular Biology of Plant Fatty Acids and Glycerolipids,* Lake Tahoe, Calif.; Abstr. P-227.

27. Rutar, V. (1989) Magic angle sample spinning NMR spectroscopy of liquids as a non-destructive method for studies of plant seeds. *J. Agric. Food Chem.*, 37: 67–70.
28. Southern E. M. (1975) Detection of specific sequences among DNA fragments separated by gel electrophoresis. *J. Mol. Biol.*, 98: 503–517.
29. Taylor, D. C., Barton, D. L., Rioux, K. P., Reed, D. W., Underhill, E. W., MacKenzie, S. L., Pomeroy, M. K. and Weber, N. (1992). Biosynthesis of Acyl Lipids Containing Very-Long Chain Fatty Acids in Microspore-Derived and Zygotic Embryos of *Brassica napus* L, Cv. Reston. *Plant Physiol.* 99: 1609–1618. NRCC No. 33523.
30. Taylor D. C., Magus, J. R, Bhella, R., Zou, J- T., MacKenzie, S. L., Giblin, E. M., Pass, E. W. and Crosby, W. L. (1993). Biosynthesis of Triacylglycerols in *Brassica napus* L. cv. Reston; Target: Trierucin, In: MacKenzie, S. L. and Taylor, D. C. (eds), *Seeds Oils for the Future,* Am. Oil Chem. Soc., Champaign, Ill., Chapter 10, pp 77–102. NRCC No. 35122.
31. Taylor, D. C., MacKenzie, S. L., McCurdy, A. R., McVetty, P. B. E., Giblin, E. M., Pass, E. W., Stone, S. J., Scarth, R., Rimmer, S. R. and Pickard, M. D. (1994) Stereospecific Analyses of Triacylglycerols from High Erucic Brassicaceae: Detection of Erucic Acid at the sn-2 Position in *Brassica oleracea* L. Genotypes. *J. Am. Oil Chem. Soc.* 71: 163–167.
32. Taylor, D. C., Giblin, E. M., Reed, D. W., Olson, D. J., Hogge L. R. and MacKenzie, S. L. (1995a) Stereospecific Analysis and Mass Spectrometry of Triacylglycerols from *Arabidopsis thaliana* (L.) Heynh. Columbia Seed. *J. Am. Oil Chem. Soc.* 72 (3): 305–308.
33. Taylor, D. C., Barton, D. L., Giblin, E. M., MacKenzie, S. L., van den Berg, C. G. J. and McVetty, P. B. E. (1995b) Developing seeds of a *Brassica oleracea* Breeding Line Possess a Lyso-Phosphatidic Acid Acyltransferase Capable of utilizing Erucoyl-CoA and Accumulate Triacylglycerols Containing Erucic Acid in the sn-2 Position. *Plant Physiology,* 109: 409–420.
34. Van Blokland, R., De Lange, P., Mol, J. N. M., and Kooter, J. M. (1993) Modulation of gene expression in plants by antisense genes. In: Lebleu, B. (ed) *Antisense research and applications.* CRC Press, Boca Raton, Fla., pp 125–148.
35. Voelker, T. A., Worrell, A. C., Anderson, L., Bleibaum, J., Fan, C., Hawkins, D. J., Radke, S. E., and Davies, H. M. (1992) Fatty acid biosynthesis redirected to medium chains in transgenic oilseed plants. *Science* 257: 72–74.
36. Voelker, T. A., Hayes, T. R., Cramner, A. M., Turner, J. C., and Davies, H. M. (1996) Genetic engineering of a quantitative trait: metabolic and genetic parameters influencing the accumulation of laurate in rapeseed. *The Plant Journal* 9: 229–241.
37. Stymne, S. and Stobart A. K. (1987) Triacylglycerol biosynthesis. In: Stumpf, P. K. and Conn, E. E. (eds), The Biochemistry of Plants: Lipids, Vol. 9. Academic Press, New York, pp. 175–214.
38. Ohlrogge, J. B., Browse, J. and Somerville, C. R. (1991) The Genetics of Plant Lipids, Biochem. Biophys. Acta 1082:1–26.
39. Murphy, D. J. (1993) Plant Lipids: Their Metabolism, Function, and Utilization, In: Lea, P. J. and Leegood, R. C. (eds), Plant Biochemistry and Molecular Biology. John Wiley & Sons, New York. pp. 113–128.
40. Ohlrogge, J. B. and Browse, J. (1985) Lipid Biosynthesis. The Plant Cell, 7:957–970.

Patents of Interest to the Current Invention
1. Calgene, Inc. (Patent Applicant); Inventors: Davies, H. M., Hawkins, D., Nelsen, J., Lassner, M.; PCT patent publication WO 95/27791. "Plant lysophosphatidic acid acyltransferases."
2. Calgene Inc. has been granted a US patent (WPI Accession No. 91-348069-48; *Biotech Patent News,* 6, 1992) governing the use of anti-sense technology in plant cells.
3. duPont de Nemours and Company (Patent Applicant; Inventors: Lightner, J. E., Okuley, J. J.; PCT patent publication WO 94/11516; Published European patent application EP 0668919. "Genes for microsomal delta-12 fatty acid desaturases and related enzymes from plants."
4. Nickerson Biocem. Ltd. (Patent Assignee); Inventors: Slabas A. R. and Brown, A. P.; PCT patent publication WO 94/13814; European patent publication EP 0673424. "DNA encoding 2-acyltransferases."
5. University of Kentucky Research Foundation (Patent Applicant); Authors: Dickson, R. et al.; unpublished pending U.S. patent application Ser. No. 434,039. "A technique for specifying the fatty acid at the sn-2 position of acylglycerol lipids."

We claim:

1. A transgenic plant characterized in that said plant has a genome incorporating an expressible yeast SLC1-1 gene having the nucleotide sequence of SEQ ID NO:1 or an expressible yeast SLC1 gene having the nucleotide sequence of SEQ ID NO:3.

2. A plant according to claim 1 characterized in that said plant consistently exhibits improved seed oil yield and/or a different seed oil composition compared with control plants of the same genotype grown under identical environmental conditions and at the same time, that do not contain either SEQ ID NO:1 or SEQ ID NO:3.

3. A plant according to claim 1 characterized in that said plant produces non-edible oils.

4. A plant according to claim 1, characterized in that said plant produces edible oil.

5. A plant according to claim 1, characterized in that said plant is *Arabidopsis thaliana* modified to include said SLC1-1 gene or said SLC1 gene.

6. A plant according to claim 1, characterized in that said plant is a member of the Brassicaceae modified to include said SLC1-1 gene or said SLC1 gene.

7. A plant according to claim 1, characterized in that said plant is *Brassica napus* modified to include said SLC1-1 gene or said SLC1 gene.

8. A plant according to claim 1, characterized in that said plant is *Brassica carinata* modified to include said SLC1-1 gene or said SLC1 gene.

9. A plant according to claim 1, characterized in that said plant is selected from the group consisting of borage (Borago spp.), canola, castor (*Ricinus communis*), cocoa bean (*Theobroma cacao*), corn (*Zea Mays*), cotton (Gossypium spp), Crambe spp., Cuphea spp., flax (Linum spp.), Lesquerella and Limnanthes spp., linola, nasturtium (Tropaeolum spp.), Oenothera spp., olive (Olea spp.), palm (Elaeis spp.), peanut (Arachis spp.), rapeseed, safflower (Carthamus spp.), soybean (Glycine and Soja spp.), sunflower (Helianthus spp.), tobacco (Nicotiana spp.) and Vernonia spp., modified to include said SLC1-1 gene or said SLC1 gene.

10. A plant according to claim 1, containing an endogenous gene that encodes lyso-phosphatidic acid acyltransferase, characterized in that expression of said endogenous gene has been suppressed.

11. A seed of a transgenic plant characterized in that said seed has a genome incorporating an expressible yeast SLC1-1 gene having the nucleotide sequence of SEQ ID NO:1 or an expressible yeast SLC1 gene having the nucleotide sequence of SEQ ID NO:3.

12. A seed according to claim 11 characterized in that said seed produces non-edible oils.

13. A seed according to claim 11 characterized in that said seed produces edible oil.

14. A seed according to claim 11 characterized in that said seed is a seed of *Arabidopsis thaliana* modified to include said gene SLC1-1 gene or said SLC1.

15. A seed according to claim 11 characterized in that said seed is a seed of a member of the Brassicaceae modified to include said SLC1-1 gene or said SLC1 gene.

16. A seed according to claim 11 characterized in that said seed is a seed of *Brassica napus* modified to include said SLC1-1 gene or said SLC1 gene.

17. A seed according to claim 11 characterized in that said seed is a seed of *Brassica carinata* modified to include said SLC1-1 gene or said SLC1 gene.

18. A plant according to claim 11 characterized in that said seed is a seed of a plant selected from the group consisting of borage (Borago spp.), castor (*Ricinus communis*), cocoa bean (*Theobroma cacao*), corn (*Zea Mays*), cotton (Gossypium spp), Crambe spp., Cuphea spp., flax (Linum spp.), Lesquerella and Limnanthes spp., nasturtium (Tropaeolum spp.), Oenothera spp., olive (Olea spp.), palm (Elaeis spp.), peanut (Arachis spp.), safflower (Carthamus spp.), soybean (Glycine and Soja spp.), sunflower (Helianthus spp.), tobacco (Nicotiana spp.) and Vernonia spp., modified to include said SLC1-1 gene or said SLC1 gene.

19. A seed according to claim 11 containing an endogenous gene that encodes lyso-phosphatidic acid acyltransferase, characterized in that expression of said endogenous gene has been suppressed.

20. Plasmid pSLC1-1/pRD400 (ATCC 97545).

21. *Agrobacterium tumefaciens* strain GV3101 characterized in that, into said strain has been introduced a yeast SLC1-1 gene having the nucleotide sequence of SEQ ID NO:1.

22. A method of producing a transgenic plant, characterized in that an expressible yeast SLC1-1 gene having the nucleotide sequence of SEQ ID NO:1 or an expressible yeast SLC1 gene having the nucleotide sequence of SEQ ID NO:3, is introduced into the genome of said plant.

23. A method according to claim 22 when said plant contains an endogenous gene that encodes lyso-phosphatidic acid acyltransferase, further characterized by suppressing expression of said endogenous gene that encodes lyso-phosphatidic acid acyltransferase already present in the transfenic plant.

24. A method of producing a transformed plant having improved resistance to biological and environmental stresses, compared with control plants of the same genotype grown under identical environmental conditions and at the same time, characterized by introducing into the genome of said plant an expressible yeast SLC1-1 gene or SLC1.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 947 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: Saccharomyces cerevisiae (ix) FEATURE:
       (A) NAME/KEY: CDS
       (B) LOCATION:1..909

(xi) SEQUENCE DESCRIPTION: SEQ ID NO: 1:

```
ATG AGT GTG ATA GGT AGG TTC TTG TAT TAC TTG AGG TCC GTG TTG GTC        48
Met Ser Val Ile Gly Arg Phe Leu Tyr Tyr Leu Arg Ser Val Leu Val
 1               5                  10                  15

GTA CTG GCG CTT GCA GGC TGT GGC TTT TAC GGT GTA ATC GCC TCT ATC        96
Val Leu Ala Leu Ala Gly Cys Gly Phe Tyr Gly Val Ile Ala Ser Ile
             20                  25                  30

CTT TGC ACG TTA ATC GGT AAG CAA CAT TTG GCT CTG TGG ATT ACT GCG       144
Leu Cys Thr Leu Ile Gly Lys Gln His Leu Ala Leu Trp Ile Thr Ala
         35                  40                  45

CGT TGT TTT TAC CAT GTC ATG AAA TTG ATG CTT GGC CTT GAC GTC AAG       192
Arg Cys Phe Tyr His Val Met Lys Leu Met Leu Gly Leu Asp Val Lys
     50                  55                  60

GTC GTT GGC GAG GAG AAT TTG GCC AAG AAG CCA TAT ATT ATG ATT GCC       240
Val Val Gly Glu Glu Asn Leu Ala Lys Lys Pro Tyr Ile Met Ile Ala
 65                  70                  75                  80

AAT CAC CAA TCC ACC TTG GAT ATC TTC ATG TTA GGT AGG ATT TTC CCC       288
Asn His Gln Ser Thr Leu Asp Ile Phe Met Leu Gly Arg Ile Phe Pro
                 85                  90                  95

CCT GGT TGC ACA GTT ACT GCC AAG AAG TCT TTG AAA TAC GTC CCC TTT       336
Pro Gly Cys Thr Val Thr Ala Lys Lys Ser Leu Lys Tyr Val Pro Phe
            100                 105                 110

CTG GGT TGG TTC ATG GCT TTG AGT GGT ACA TAT TTC TTA GAC AGA TCT       384
Leu Gly Trp Phe Met Ala Leu Ser Gly Thr Tyr Phe Leu Asp Arg Ser
        115                 120                 125

AAA AGG CAA GAA GCC ATT GAC ACC TTG AAT AAA GGT TTA GAA AAT GTT       432
Lys Arg Gln Glu Ala Ile Asp Thr Leu Asn Lys Gly Leu Glu Asn Val
    130                 135                 140

AAG AAA AAC AAG CGT GCT CTA TGG GTT TTT CCT GAG GGT ACC AGG TCT       480
Lys Lys Asn Lys Arg Ala Leu Trp Val Phe Pro Glu Gly Thr Arg Ser
145                 150                 155                 160

TAC ACG AGT GAG CTG ACA ATG TTG CCT TTC AAG AAG GGT GCT TTC CAT       528
Tyr Thr Ser Glu Leu Thr Met Leu Pro Phe Lys Lys Gly Ala Phe His
                165                 170                 175

TTG GCA CAA CAG GGT AAG ATC CCC ATT GTT CCA GTG GTT GTT TCC AAT       576
Leu Ala Gln Gln Gly Lys Ile Pro Ile Val Pro Val Val Val Ser Asn
            180                 185                 190

ACC AGT ACT TTA GTA AGT CCT AAA TAT GGG GTC TTC AAC AGA GGC TGT       624
Thr Ser Thr Leu Val Ser Pro Lys Tyr Gly Val Phe Asn Arg Gly Cys
        195                 200                 205

ATG ATT GTT AGA ATT TTA AAA CCT ATT TCA ACC GAG AAC TTA ACA AAG       672
Met Ile Val Arg Ile Leu Lys Pro Ile Ser Thr Glu Asn Leu Thr Lys
    210                 215                 220

GAC AAA ATT GGT GAA TTT GCT GAA AAA GTT AGA GAT CAA ATG GTT GAC       720
Asp Lys Ile Gly Glu Phe Ala Glu Lys Val Arg Asp Gln Met Val Asp
225                 230                 235                 240

ACT TTG AAG GAG ATT GGC TAC TCT CCC GCC ATC AAC GAT ACA ACC CTC       768
Thr Leu Lys Glu Ile Gly Tyr Ser Pro Ala Ile Asn Asp Thr Thr Leu
                245                 250                 255

CCA CCA CAA GCT ATT GAG TAT GCC GCT CTT CAA CAT GAC AAG AAA GTG       816
Pro Pro Gln Ala Ile Glu Tyr Ala Ala Leu Gln His Asp Lys Lys Val
            260                 265                 270

AAC AAG AAA ATC AAG AAT GAG CCT GTG CCT TCT GTC AGC ATT AGC AAC       864
Asn Lys Lys Ile Lys Asn Glu Pro Val Pro Ser Val Ser Ile Ser Asn
        275                 280                 285

GAT GTC AAT ACC CAT AAC GAA GGT TCA TCT GTA AAA AAG ATG CAT           909
Asp Val Asn Thr His Asn Glu Gly Ser Ser Val Lys Lys Met His
    290                 295                 300
```

TAAGCCACCA CCACATTTTT AGAGTAGTAT ATAGACCC            947

(2) INFORMATION FOR SEQ ID NO: 2:

(i) SEQUENCE CHARACTERISTICS:
　　　　(A) LENGTH: 303 amino acids
　　　　(B) TYPE: amino acid
　　　　(D) TOPOLOGY: linear (ii) MOLECULE TYPE: protein (xi) SEQUENCE DESCRIPTION: SEQ ID NO: 2:

```
Met Ser Val Ile Gly Arg Phe Leu Tyr Tyr Leu Arg Ser Val Leu Val
 1               5                  10                  15

Val Leu Ala Leu Ala Gly Cys Gly Phe Tyr Gly Val Ile Ala Ser Ile
        20                  25                  30

Leu Cys Thr Leu Ile Gly Lys Gln His Leu Ala Leu Trp Ile Thr Ala
        35                  40                  45

Arg Cys Phe Tyr His Val Met Lys Leu Met Leu Gly Leu Asp Val Lys
    50                  55                  60

Val Val Gly Glu Glu Asn Leu Ala Lys Lys Pro Tyr Ile Met Ile Ala
65                  70                  75                  80

Asn His Gln Ser Thr Leu Asp Ile Phe Met Leu Gly Arg Ile Phe Pro
                85                  90                  95

Pro Gly Cys Thr Val Thr Ala Lys Lys Ser Leu Lys Tyr Val Pro Phe
                100                 105                 110

Leu Gly Trp Phe Met Ala Leu Ser Gly Thr Tyr Phe Leu Asp Arg Ser
                115                 120                 125

Lys Arg Gln Glu Ala Ile Asp Thr Leu Asn Lys Gly Leu Glu Asn Val
130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
                165                 170                 175

Leu Ala Gln Gln Gly Lys Ile Pro Ile Val Pro Val Val Val Ser Asn
                180                 185                 190

Thr Ser Thr Leu Val Ser Pro Lys Tyr Gly Val Phe Asn Arg Gly Cys
                195                 200                 205

Met Ile Val Arg Ile Leu Lys Pro Ile Ser Thr Glu Asn Leu Thr Lys
        210                 215                 220

Asp Lys Ile Gly Glu Phe Ala Glu Lys Val Arg Asp Gln Met Val Asp
225                 230                 235                 240

Thr Leu Lys Glu Ile Gly Tyr Ser Pro Ala Ile Asn Asp Thr Thr Leu
                245                 250                 255

Pro Pro Gln Ala Ile Glu Tyr Ala Ala Leu Gln His Asp Lys Lys Val
                260                 265                 270

Asn Lys Lys Ile Lys Asn Glu Pro Val Pro Ser Val Ser Ile Ser Asn
            275                 280                 285

Asp Val Asn Thr His Asn Glu Gly Ser Ser Val Lys Lys Met His
        290                 295                 300
```

(2) INFORMATION FOR SEQ ID NO: 3:

(i) SEQUENCE CHARACTERISTICS:
　　　　(A) LENGTH: 947 base pairs
　　　　(B) TYPE: nucleic acid
　　　　(C) STRANDEDNESS: single
　　　　(D) TOPOLOGY: linear (ii) MOLECULE TYPE: DNA (genomic)

(ix) FEATURE:
    (A) NAME/KEY: CDS
    (B) LOCATION:1..909

(xi) SEQUENCE DESCRIPTION: SEQ ID NO: 3:

```
ATG AGT GTG ATA GGT AGG TTC TTG TAT TAC TTG AGG TCC GTG TTG GTC        48
Met Ser Val Ile Gly Arg Phe Leu Tyr Tyr Leu Arg Ser Val Leu Val
 1               5                  10                  15

GTA CTG GCG CTT GCA GGC TGT GGC TTT TAC GGT GTA ATC GCC TCT ATC        96
Val Leu Ala Leu Ala Gly Cys Gly Phe Tyr Gly Val Ile Ala Ser Ile
             20                  25                  30

CTT TGC ACG TTA ATC GGT AAG CAA CAT TTG GCT CAG TGG ATT ACT GCG       144
Leu Cys Thr Leu Ile Gly Lys Gln His Leu Ala Gln Trp Ile Thr Ala
         35                  40                  45

CGT TGT TTT TAC CAT GTC ATG AAA TTG ATG CTT GGC CTT GAC GTC AAG       192
Arg Cys Phe Tyr His Val Met Lys Leu Met Leu Gly Leu Asp Val Lys
     50                  55                  60

GTC GTT GGC GAG GAG AAT TTG GCC AAG AAG CCA TAT ATT ATG ATT GCC       240
Val Val Gly Glu Glu Asn Leu Ala Lys Lys Pro Tyr Ile Met Ile Ala
 65                  70                  75                  80

AAT CAC CAA TCC ACC TTG GAT ATC TTC ATG TTA GGT AGG ATT TTC CCC       288
Asn His Gln Ser Thr Leu Asp Ile Phe Met Leu Gly Arg Ile Phe Pro
                 85                  90                  95

CCT GGT TGC ACA GTT ACT GCC AAG AAG TCT TTG AAA TAC GTC CCC TTT       336
Pro Gly Cys Thr Val Thr Ala Lys Lys Ser Leu Lys Tyr Val Pro Phe
            100                 105                 110

CTG GGT TGG TTC ATG GCT TTG AGT GGT ACA TAT TTC TTA GAC AGA TCT       384
Leu Gly Trp Phe Met Ala Leu Ser Gly Thr Tyr Phe Leu Asp Arg Ser
        115                 120                 125

AAA AGG CAA GAA GCC ATT GAC ACC TTG AAT AAA GGT TTA GAA AAT GTT       432
Lys Arg Gln Glu Ala Ile Asp Thr Leu Asn Lys Gly Leu Glu Asn Val
    130                 135                 140

AAG AAA AAC AAG CGT GCT CTA TGG GTT TTT CCT GAG GGT ACC AGG TCT       480
Lys Lys Asn Lys Arg Ala Leu Trp Val Phe Pro Glu Gly Thr Arg Ser
145                 150                 155                 160

TAC ACG AGT GAG CTG ACA ATG TTG CCT TTC AAG AAG GGT GCT TTC CAT       528
Tyr Thr Ser Glu Leu Thr Met Leu Pro Phe Lys Lys Gly Ala Phe His
                165                 170                 175

TTG GCA CAA CAG GGT AAG ATC CCC ATT GTT CCA GTG GTT GTT TCC AAT       576
Leu Ala Gln Gln Gly Lys Ile Pro Ile Val Pro Val Val Val Ser Asn
            180                 185                 190

ACC AGT ACT TTA GTA AGT CCT AAA TAT GGG GTC TTC AAC AGA GGC TGT       624
Thr Ser Thr Leu Val Ser Pro Lys Tyr Gly Val Phe Asn Arg Gly Cys
        195                 200                 205

ATG ATT GTT AGA ATT TTA AAA CCT ATT TCA ACC GAG AAC TTA ACA AAG       672
Met Ile Val Arg Ile Leu Lys Pro Ile Ser Thr Glu Asn Leu Thr Lys
    210                 215                 220

GAC AAA ATT GGT GAA TTT GCT GAA AAA GTT AGA GAT CAA ATG GTT GAC       720
Asp Lys Ile Gly Glu Phe Ala Glu Lys Val Arg Asp Gln Met Val Asp
225                 230                 235                 240

ACT TTG AAG GAG ATT GGC TAC TCT CCC GCC ATC AAC GAT ACA ACC CTC       768
Thr Leu Lys Glu Ile Gly Tyr Ser Pro Ala Ile Asn Asp Thr Thr Leu
                245                 250                 255

CCA CCA CAA GCT ATT GAG TAT GCC GCT CTT CAA CAT GAC AAG AAA GTG       816
Pro Pro Gln Ala Ile Glu Tyr Ala Ala Leu Gln His Asp Lys Lys Val
            260                 265                 270

AAC AAG AAA ATC AAG AAT GAG CCT GTG CCT TCT GTC AGC ATT AGC AAC       864
Asn Lys Lys Ile Lys Asn Glu Pro Val Pro Ser Val Ser Ile Ser Asn
```

```
            275                 280                 285
GAT GTC AAT ACC CAT AAC GAA GGT TCA TCT GTA AAA AAG ATG CAT          909
Asp Val Asn Thr His Asn Glu Gly Ser Ser Val Lys Lys Met His
290                 295                 300

TAAGCCACCA CCACATTTTT AGAGTAGTAT ATAGACCC                             947
```

(2) INFORMATION FOR SEQ ID NO: 4:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ser Val Ile Gly Arg Phe Leu Tyr Tyr Leu Arg Ser Val Leu Val
 1               5                  10                  15

Val Leu Ala Leu Ala Gly Cys Gly Phe Tyr Gly Val Ile Ala Ser Ile
                 20                  25                  30

Leu Cys Thr Leu Ile Gly Lys Gln His Leu Ala Gln Trp Ile Thr Ala
             35                  40                  45

Arg Cys Phe Tyr His Val Met Lys Leu Met Leu Gly Leu Asp Val Lys
         50                  55                  60

Val Val Gly Glu Glu Asn Leu Ala Lys Lys Pro Tyr Ile Met Ile Ala
 65                  70                  75                  80

Asn His Gln Ser Thr Leu Asp Ile Phe Met Leu Gly Arg Ile Phe Pro
                 85                  90                  95

Pro Gly Cys Thr Val Thr Ala Lys Lys Ser Leu Lys Tyr Val Pro Phe
            100                 105                 110

Leu Gly Trp Phe Met Ala Leu Ser Gly Thr Tyr Phe Leu Asp Arg Ser
        115                 120                 125

Lys Arg Gln Glu Ala Ile Asp Thr Leu Asn Lys Gly Leu Glu Asn Val
130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
                165                 170                 175

Leu Ala Gln Gln Gly Lys Ile Pro Ile Val Pro Val Val Val Ser Asn
            180                 185                 190

Thr Ser Thr Leu Val Ser Pro Lys Tyr Gly Val Phe Asn Arg Gly Cys
        195                 200                 205

Met Ile Val Arg Ile Leu Lys Pro Ile Ser Thr Glu Asn Leu Thr Lys
    210                 215                 220

Asp Lys Ile Gly Glu Phe Ala Glu Lys Val Arg Asp Gln Met Val Asp
225                 230                 235                 240

Thr Leu Lys Glu Ile Gly Tyr Ser Pro Ala Ile Asn Asp Thr Thr Leu
                245                 250                 255

Pro Pro Gln Ala Ile Glu Tyr Ala Ala Leu Gln His Asp Lys Lys Val
            260                 265                 270

Asn Lys Lys Ile Lys Asn Glu Pro Val Pro Ser Val Ser Ile Ser Asn
        275                 280                 285

Asp Val Asn Thr His Asn Glu Gly Ser Ser Val Lys Lys Met His
    290                 295                 300
```

(2) INFORMATION FOR SEQ ID NO: 5:

```
    (i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

AGAGAGAGGG ATCCATGAGT GTGATAGGTA GG                                    32

(2) INFORMATION FOR SEQ ID NO: 6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GAGGAAGAAG GATCCGGGTC TATATACTAC TCT                                   33
```